(12) United States Patent
Salcudean et al.

(10) Patent No.: US 11,510,652 B2
(45) Date of Patent: Nov. 29, 2022

(54) ULTRASOUND SHEAR WAVE VIBRO-ELASTOGRAPHY OF THE ABDOMEN

(71) Applicant: THE UNIVERSITY OF BRITISH COLUMBIA, Vancouver (CA)

(72) Inventors: Septimiu Salcudean, Vancouver (CA); Robert Rohling, Vancouver (CA); Mohammad Honarvar, Vancouver (CA); Julio Raul Lobo, Vancouver (CA); Caitlin Marie Schneider, Vancouver (CA)

(73) Assignee: The University of British Columbia, Vancouver (CA)

( * ) Notice: Subject to any disclaimer, the term of this patent is extended or adjusted under 35 U.S.C. 154(b) by 220 days.

(21) Appl. No.: 16/226,401

(22) Filed: Dec. 19, 2018

(65) Prior Publication Data

US 2019/0192119 A1   Jun. 27, 2019

Related U.S. Application Data

(63) Continuation of application No. PCT/CA2017/050804, filed on Jun. 30, 2017.
(Continued)

(51) Int. Cl.
*A61B 8/08*   (2006.01)
*A61B 8/14*   (2006.01)
(Continued)

(52) U.S. Cl.
CPC ............... *A61B 8/485* (2013.01); *A61B 8/08* (2013.01); *A61B 8/085* (2013.01); *A61B 8/14* (2013.01);
(Continued)

(58) Field of Classification Search
CPC ........... A61B 8/485; A61B 8/08; A61B 8/085; A61B 8/14; A61B 8/4209; A61B 8/4218;
(Continued)

(56) References Cited

U.S. PATENT DOCUMENTS 5,099,848 A * 3/1992 Parker ................... A61B 8/0825
600/441
5,107,837 A   4/1992 Ophir et al.
(Continued)

FOREIGN PATENT DOCUMENTS

CN       103110432 A     5/2013
DE    102011089401 A1    6/2013
(Continued)

OTHER PUBLICATIONS

Baghani, Ali, A wave equation approach to ultrasound elastography, Vancouver : University of British Columbia Library, Jan. 12, 2010, 10.14288/1.0070904 (Year: 2010).*
(Continued)

*Primary Examiner* — Amelie R Davis
*Assistant Examiner* — John Denny Li
(74) *Attorney, Agent, or Firm* — Oyen Wiggs Green & Mutala LLP

(57) ABSTRACT

A system useful for performing ultrasound elastography of organs such as the liver allows efficient and robust data acquisition. The system may be applied to perform real-time, noninvasive ultrasound imaging of the liver in humans. Steady-state, shear wave absolute elastography is used to measure the Young's modulus of the liver tissue. This method involves the use of an external exciter or vibrator to shake the tissue and generate a shear wave. Accurate placement of an ultrasound transducer facilitates measurement of the tissue motion due to the shear wave. The stiffness of tissues in the region being imaged may be computed from
(Continued)

the measured tissue motions. The following innovations address both vibrator and transducer placement, as well as some specific methods to ensure adequate wave propagation, in order to obtain accurate and consistent measurements.

22 Claims, 15 Drawing Sheets

Related U.S. Application Data

(60) Provisional application No. 62/357,254, filed on Jun. 30, 2016.

(51) Int. Cl.
*A61B 8/00* (2006.01)
*G01S 7/52* (2006.01)

(52) U.S. Cl.
CPC .......... *A61B 8/4209* (2013.01); *A61B 8/4218* (2013.01); *A61B 8/4227* (2013.01); *A61B 8/461* (2013.01); *A61B 8/483* (2013.01); *A61B 8/54* (2013.01); *G01S 7/52042* (2013.01)

(58) Field of Classification Search
CPC ....... A61B 8/4227; A61B 8/461; A61B 8/483; A61B 8/54; G01S 7/52042
See application file for complete search history.

(56) References Cited

U.S. PATENT DOCUMENTS

| | | | |
|---|---|---|---|
| 5,825,186 A | | 10/1998 | Ehman et al. |
| 5,977,770 A | | 11/1999 | Ehman |
| 6,037,774 A | | 3/2000 | Femlee et al. |
| 6,511,427 B1 | * | 1/2003 | Sliwa, Jr. ............. A61B 5/4869 600/438 |
| 7,444,875 B1 | * | 11/2008 | Wu ........................ A61B 8/08 73/602 |
| 2003/0073895 A1 | * | 4/2003 | Nields ................... A61B 6/469 600/407 |
| 2004/0077978 A1 | | 4/2004 | Nelson et al. |
| 2004/0225215 A1 | | 11/2004 | Querleux et al. |
| 2005/0119568 A1 | | 6/2005 | Salcudean et al. |
| 2006/0106313 A1 | | 5/2006 | Hobson |
| 2006/0159293 A1 | * | 7/2006 | Azima .................. G06F 1/1616 381/152 |
| 2007/0205785 A1 | | 9/2007 | Nilsson |
| 2008/0200811 A1 | | 8/2008 | Wakabayashi et al. |
| 2009/0036776 A1 | | 2/2009 | Masuda et al. |
| 2010/0256530 A1 | * | 10/2010 | Varghese ............. A61B 5/0051 600/587 |
| 2014/0163374 A1 | * | 6/2014 | Ogasawara .......... A61B 8/4236 600/443 |
| 2014/0330122 A1 | | 11/2014 | Baghani et al. |
| 2016/0038119 A1 | * | 2/2016 | Desjardins ......... A61B 17/3403 600/424 |
| 2016/0157828 A1 | * | 6/2016 | Sumi .................... G01N 29/262 702/189 |
| 2016/0345938 A1 | * | 12/2016 | Tanter .................. A61B 8/0883 |

FOREIGN PATENT DOCUMENTS

| | | |
|---|---|---|
| JP | 2003-230543 A | 8/2003 |
| JP | 2013-081764 A | 5/2013 |
| JP | 2015-524740 A | 8/2015 |
| JP | 2015-181767 A | 10/2015 |
| WO | 2016067072 A1 | 5/2016 |
| WO | 2016085341 A1 | 6/2016 |

OTHER PUBLICATIONS

Tzschatsch, H. et al., "Time-harmonic multifrequency elastography of the human liver", Physics in Medicine and Biology, Institute of Physics Publishing, Bristol GB, vol. 59, No. 7, Mar. 10, 2014, pp. 1641-1654 (D1).
Ipek-Ugay, S. et al., "Time Harmonic Elastography Reveals Sensitivity of Liver Stiffness to Water Ingestion", Ultrasound in Medicine and Biology, vol. 42, No. 6, Jun. 1, 2016, pp. 1289-1294.
Huwart, L. et al., "Liver fibrosis: noninvasive assessment with MR elastography", NMR in Biomedicine 2006, pp. 173-179.
Yin, M. et al., "Assessment of Hepatic Fibrosis With Magnetic Resonance Elastography", Clinical Gastroenterology and Hepatology 2007; 5:1207-1213.
Sinkus, R. et al., "Viscoelastic shear properties of in vivo breast lesions measured by MR elastography", Magnetic Resonance Imaging 23 (2005) 159-165.

* cited by examiner

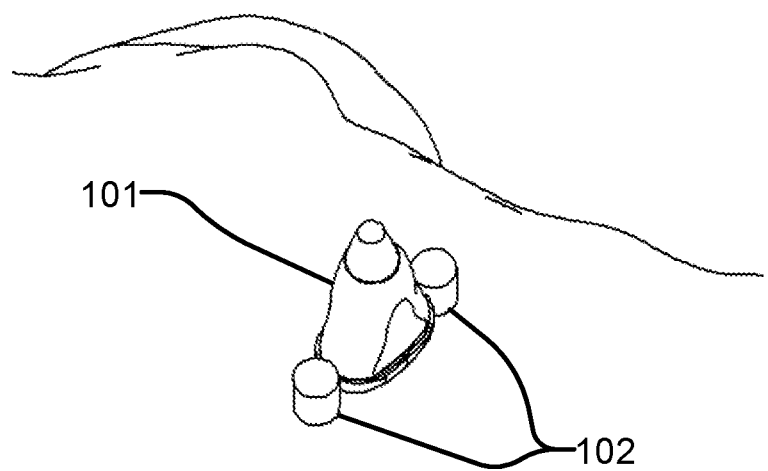
FIG. 7A
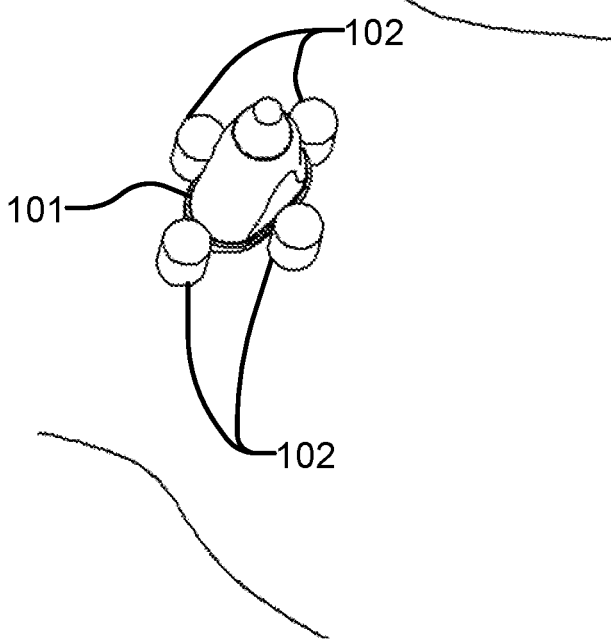
FIG. 7B

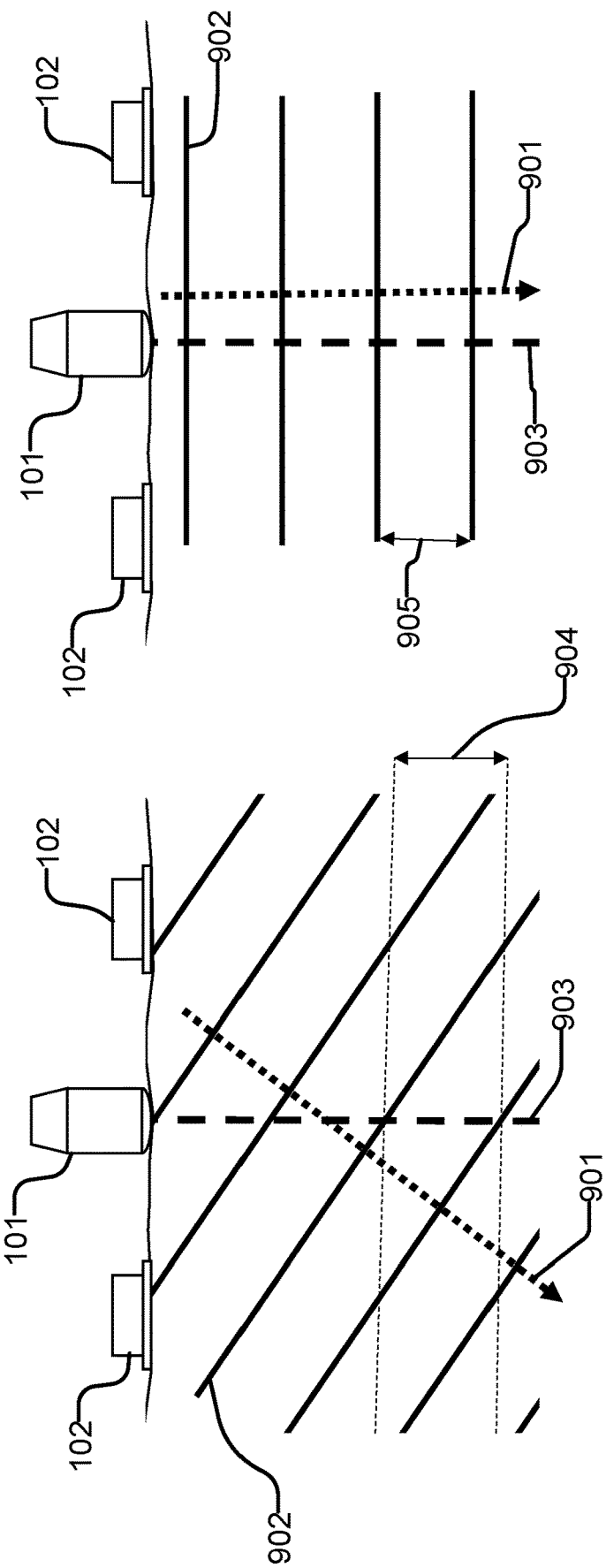

ULTRASOUND SHEAR WAVE VIBRO-ELASTOGRAPHY OF THE ABDOMEN

CROSS-REFERENCE TO RELATED APPLICATIONS

This application is a continuation of PCT International Application No. PCT/CA2017/050804 filed 30 Jun. 2017, which claims the benefit under 35 U.S.C. § 119 of U.S. Application No. 62/357,254 filed 30 Jun. 2016, both of which are entitled ULTRASOUND SHEAR WAVE VIBRO-ELASTOGRAPHY OF THE ABDOMEN and both of which are hereby incorporated herein by reference for all purposes.

FIELD OF THE INVENTION

This invention relates to medical imaging, in particular, medical imaging that applies shear-wave elastography. The present technology may provide information characterizing the mechanical properties of abdominal organs such as the liver, kidneys, spleen, bladder wall etc. Example applications of the present technology include imaging of the abdomen, including, for example, the liver.

BACKGROUND OF THE INVENTION

Medical imaging is used in many applications to determine the composition of tissues. In medical images the intensity and/or color of the image may be a function of some parameter of the tissue composition. For example: computed tomography (CT) displays to the user the absorption of X-rays in the body; ultrasound displays the echo pattern produced in response to a pulsed sound wave.

Mechanical properties of tissue are of particular interest. Changes in the mechanical properties of certain tissues can indicate disease. Changes in the mechanical properties of tissue can also indicate the success or failure of therapy. Traditional diagnostic methods have relied on manual palpation to discriminate between healthy and diseased tissues. For example, the palpation of stiffer tissue is often the first step in the diagnosis of breast cancer and liver disease such as cirrhosis.

Elastography is a medical imaging technique that aims to depict elasticity, a mechanical property of tissue. Elasticity is also referred to as stiffness, or the inverse of compliance. Advanced elastography techniques can also measure the dynamic viscoelastic properties of tissue, such as viscosity and relaxation time. In elastographic imaging, a mechanical excitation is applied in the proximity of the tissue of interest (e.g., the prostate) and the resulting deformation of the tissue is measured. The resulting deformation may be measured with ultrasound (ultrasound elastography or USE) or Magnetic Resonance Imaging (magnetic resonance elastography or MRE). The deformation is post-processed to extract information such as viscoelastic properties (e.g., shear modulus and viscosity). The deformation or tissue strain, or alternatively, the intrinsic mechanical properties of tissue are then displayed as a map of stiffness (or other meaningful mechanical property) of the imaged object.

Some clinical uses of elastography are described in Ophir et. al., U.S. Pat. No. 5,107,837. Elastography using magnetic resonance imaging (MRI) is described in Ehman et al., U.S. Pat. No. 5,825,186 and Ehman, U.S. Pat. No. 5,977,770.

Elastography has been shown to be of clinical value for the detection and staging of hepatic (liver) fibrosis by Sinkus et. al. "Liver fibrosis: noninvasive assessment with MR elastography" in the Journal NMR in Biomedicine 2006, pages 173-179, and Ehman et. al. "Assessment of Hepatic Fibrosis With Magnetic Resonance Elastography" in the Journal of Clinical Gastroenterology and Hepatology, volume 5, Issue 10, October 2007, pages 1207-1213. Elastography imaging of the breast is described by Sinkus et. al. in "Viscoelastic shear properties of in vivo breast lesions measured by MR elastography" in the Journal of Magnetic Resonance Imaging volume 23, 2005, pages 159-165.

Quantitative elastography is an elastography technique that solves an inverse problem: calculating the stiffness in a region of interest given excitation of the tissue and measurement of resulting motion in that region. The inverse problem can be solved for either a 1D (single point) region of interest, 2D (cross-sectional planar) region of interest, or a 3D (volumetric) region of interest.

The mechanical waves induced by external exciters in most of the previous mentioned techniques vary in both space and time. The measurement system measures all one, two, or three components (x,y,z) of the displacements over the region of interest at multiple instances in time. Such measurements form a mathematical representation of the wave propagation. Given the finite speed of sound of standard pulse-echo ultrasound imaging, it is possible to exploit the steady state nature of the wave propagation to build up the mathematical representation through multiple measurements over several periods of the waves. This is usually achieved by synchronizing acquisition with the exciter that is creating the waves and assuming periodicity in the excitations.

A. Baghani et al., US2012/000779, "Elastography using ultrasound imaging of a thin volume", the entirety of which is hereby incorporated by reference for all purposes, presents a method for acquiring volumetric quantitative elastography images using suitable transducers such as, for example, matrix arrays that can electronically steer a planar beam to form a 3D volume, such as the xMATRIX™ (iU22) (Philips Healthcare, Andover, MA), or using mechanically swept linear ultrasound imaging transducers, such as the 4DL14-5/38 Linear 4D ultrasound transducer (Analogic Corporation, Richmond, BC), that move an imaging a plane in the elevational direction in order to acquire a volumetric image. In Baghani et al. the sweeping motion of the mechanically swept ultrasound transducers is synchronized with the known frequency of the tissue motion in order to generate a set of tissue displacement estimates that are regularly spaced in time and space. These displacement estimates can be used to compute elasticity images using techniques known in the art, such as the local spatial frequency estimator. The general name given to such elastography is quantitative shear wave vibro-elastography.

A range of issues arise when quantitative ultrasound shear wave vibro-elastography images are required in deep tissue that is under the ribcage. In general, the presence of the ribcage presents difficulties when using any ultrasound imaging technique since the bones obstruct the imaging field.

There remains a need for practical cost effective apparatus and methods useful for performing elastography, particularly of organs in the abdomen such as the liver.

SUMMARY

This invention provides apparatus and methods useful for shear-wave elastography. Specific example mechanical and electrical designs which allow for deep, consistent shear wave transmission into the tissue, through the ribcage are described herein. This invention also describes apparatus useful to securely support and fix ultrasound transducers such that obstructions are avoided and a large region or volume of interest is visible.

Example aspects of the invention include, without limitation:
- apparatus generating shear waves in the body of a patient;
- methods for transmitting shear waves into the body of a patient;
- methods and apparatus for controlling the direction of shear waves in a patient;
- methods and apparatus for ameliorating the effect of vibrational nodes in elastography;
- methods and apparatus for optimizing a field of shear waves for use in elastography;
- methods and apparatus for generating elastographic images;
- methods and apparatus for measuring mechanical properties such as Young's modulus, stiffness and/or viscosity of tissues of a living human or animal; and
- methods and apparatus useful for determining mechanical properties of tissues in the liver or other organ of a living human or animal.

Systems according to disclosed embodiments may be applied to perform steady-state, shear wave absolute elastography to measure the Young's modulus of the liver tissue.

According to an example aspect of the invention there is provided an apparatus for ultrasound elastography comprising: an external vibrator comprising a generally flat, stiff, patient-contacting member dimensioned to support at least a portion of the back of a patient, at least one exciter coupled to drive vibration of the patient-contacting member; an ultrasound imaging system comprising an ultrasound transducer, driving circuits operative to drive the ultrasound transducer to transmit ultrasound pulses and to receive ultrasound echo signals; a data processor configured to process the ultrasound echo signals to detect and measure motions corresponding to shear waves generated by the external vibrator.

In some embodiments the exciter comprises a mass movable relative to the patient contacting member to deliver inertial reaction forces to the patient-contacting member. The mass may be movable in a direction substantially parallel to a plane of the patient contacting member. The mass may comprise an unbalanced rotor and the exciter may comprise a motor connected to drive rotation of the rotor. The mass may comprise a counterweight and the exciter may comprise an actuator connected to reciprocate the counterweight relative to the patient-contacting member.

In some embodiments the patient-contacting member is wider in a first direction parallel to a path of reciprocating motion of the counterweight than it is in a second direction transverse to the path of reciprocating motion of the counterweight. The patient contacting member may have a length in the second direction of 30 cm or less. The patient contacting member may have a width in the range of 40 to 80 cm and a length in the range of 10 to 20 cm.

The apparatus may further comprise couplers projecting on an upper surface of the patient-contacting member, the couplers engageable against opposed sides of a patient's ribcage. The exciter may be mounted for rotation relative to the patient contacting member such that alignment of a direction along which the counterweight is reciprocatable to the patient-contacting member is adjustable. The patient contacting member may comprise a core faced on opposing sides with sheets of fiber reinforced plastic. A lower surface of the patient-contacting member may be formed with a curvature and/or a centrally-located fulcrum such that the patient contacting member can rock. The mass may movable in a direction substantially perpendicular to a plane of the patient contacting member such that inertial forces on the patient-contacting member resulting from motion of the mass cause rocking of the patient-contacting member.

In some embodiments the patient-contacting member is supported on a compliant support. The compliant support may comprise one or more pillows, one or more inflatable cushions and/or one or more springs.

In some embodiments the at least one exciter comprises a plurality of exciters. The at least one exciter may comprise a variable-frequency exciter. The variable-frequency exciter may be operable to excite vibration of the patient-contacting member having a frequency or frequencies in the range of 45 Hz to 70 Hz. The apparatus may further comprise one or more accelerometers mounted to the patient-contacting member. The apparatus may further comprise a camera mounted to the patient-contacting member.

The ultrasound transducer may be supported by a remote centre of rotation mechanism that allows rotation of an imaging plane of the ultrasound transducer without changing a point of contact of the ultrasound transducer with the patient. The remote centre of rotation mechanism may comprise a linkage coupled to a transducer support. The linkage may comprise a parallelogram linkage. The apparatus may further comprise a lock operable to fix a configuration of the remote centre of rotation mechanism. The transducer may be mounted to permit rotation of the transducer about an axis oriented generally perpendicular to a surface on which elements of an imaging array of the ultrasound transducer are located.

In some embodiments the timing of operation of the ultrasound imaging system is synchronized to vibrations of the external vibrator. In still further embodiments the ultrasound imaging system may further comprise a ultrasound imaging system clock, the at least one exciter further comprise at least one exciter clock, and the ultrasound imaging system clock and the at least one exciter clock are synchronized.

The processor may be configured to optimize shear wave direction relative to a plane of imaging by the ultrasound transducer by: processing the ultrasound echo data to determine an apparent wavelength of shear waves and adjusting one of more operating parameters of the external vibrator in a manner that causes the apparent wavelength of the shear waves to be reduced. The one or more operating parameters of the external vibrator may comprise one or more of: a frequency of operation of one or more exciters of the at least one exciter, a relative phase of operation of first and second exciters of the at least one exciter, an amplitude of operation of one or more exciters of the at least one exciter, and a direction of vibration of one or more exciters of the at least one exciter. The processor may be configured to control the one or more operating parameters of the external vibrator in real time as the orientation of the ultrasound transducer is changed to minimize the apparent wavelength of the shear waves for each orientation of the ultrasound transducer. The processor may be configured to control relative phases of a plurality of exciters of the at least one exciter to minimize the apparent wavelength of the shear waves.

In some embodiments the data processor is configured to process the echo signals to identify shear wave nodes located in a volume of interest and to control one or more operating parameters of the external vibrator in a manner that causes the nodes to move or disappear. The one or more operating parameters of the external vibrator may comprise one or more of: a frequency of operation of one or more exciters of the at least one exciter, a relative phase of operation of first and second exciters of the at least one exciter; and an amplitude of operation of one or more exciters of the at least one exciter, and a direction of vibration of one or more exciters of the at least one exciter. The data processor may be configured to identify the shear wave nodes by processing the ultrasound echo signals to identify node volumes having a predetermined size and shape within the region of interest in which a maximum tissue motion is below a threshold. The node volumes may be spherical. The node volumes may have diameters in the range of 10 mm to 25 mm.

In some embodiments the ultrasound imaging system is configured to operate in alternation between a standard ultrasound imaging mode wherein the ultrasound imaging system acquires B mode ultrasound images and an ultrasound elastography imaging mode wherein the ultrasound imaging system acquires data for elastography imaging.

In some embodiments the processor is configured to compute a measure of quality of a measured tissue displacement and to base control of the external vibrator at least in part on the measure of quality. The measure of quality may comprise a signal to noise ratio. The measure of quality may comprise determining whether a measured phasor magnitude of shear waves is above a lower threshold and below an upper threshold. Computing the measure of quality may comprise comparing spatial frequencies of tissue displacements in the vicinity of a point in a volume of interest to a predetermined range of spatial frequencies. Computing the measure of quality may comprise determining a measure of how well a time sequence of tissue displacements at a point fits a predetermined wave pattern. The predetermined wave pattern may be a sinusoidal function having a frequency equal to a vibration frequency of the external vibrator.

According to a further aspect of the invention there is provided an apparatus for ultrasound elastography comprising: an external vibrator comprising a partially rigid belt and at least one exciter coupled to the belt; an ultrasound imaging system comprising an ultrasound transducer, driving circuits operative to drive the ultrasound transducer to transmit ultrasound pulses and to receive ultrasound echo signals; a data processor configured to process the ultrasound echo signals to detect and measure motions corresponding to shear waves generated by the external vibrator. In some embodiments the at least one exciter comprises a plurality of exciters.

According to a further aspect of the invention there is provided an apparatus for ultrasound elastography comprising: an ultrasound imaging system comprising an ultrasound transducer, driving circuits operative to drive the ultrasound transducer to transmit ultrasound pulses and to receive ultrasound echo signals, and at least one exciter coupled to the ultrasound transducer; a data processor configured to process the ultrasound echo signals to detect and measure motions corresponding to shear waves generated by the external vibrator. In some embodiments of the invention the at least one exciter substantially encircles the ultrasound transducer.

According to a further aspect of the invention there is provided a method for performing elastography, the method comprising: generating shear waves in a material by vibrating a patient-contacting member on which the material is lying and obtaining ultrasound echo data corresponding to a volume of interest in the material; processing ultrasound echo data to determine motions of the material resulting from the shear waves within the volume of interest and processing the motions of the material to determine an apparent wavelength of the shear waves in a plane corresponding to the ultrasound echo data; aligning a direction of motion of the shear waves in the plane corresponding to the ultrasound echo data by adjusting a first set of one or more parameters of the vibrating to minimize the apparent wavelength.

In some embodiments the material is tissues within the abdomen of a human or animal subject. All or part of the volume of interest may be located within the liver of the human or animal subject. The method may further comprise processing the motions of the material to identify nodes in the shear waves within the volume of interest and moving or eliminating one or more of the nodes by adjusting a second set of one or more parameters of the vibrating.

An example system comprises: a mechanical vibrator or exciter in contact with the patient, a belt and support for the exciter; an ultrasound transducer support and positioning system; and a control system comprising software and hardware configured to interpret tissue motion and control the excitation signal. The vibrator exciter is operable to shake the imaging region.

Another aspect of the invention provides methods for performing elastography imaging of a human liver using apparatus as described herein. In some embodiments an ultrasound transducer is placed between ribs of the human subject and the method involves operating the ultrasound imaging system to detect and measure motions corresponding to shear waves generated by an external vibrator in tissues of the liver of the human subject. In some example embodiments the human subject lies on the external vibrator. The external vibrator may have an extended surface and may be positioned proximate the liver of the human subject. In some embodiments the surface of the external vibrator is caused to vibrate in a horizontal direction at a frequency in the range of 40 Hz to 75 Hz. In some embodiments the horizontal direction may be generally at right angles to the spine of the human subject. In some embodiments the external vibrator is located between the human subject and the mattress of a bed on which the human subject is lying.

Further aspects and example embodiments are illustrated in the accompanying drawings and/or described in the following description.

BRIEF DESCRIPTION OF THE FIGURES

The accompanying drawings illustrate non-limiting example embodiments of the invention.

FIG. 7A is a diagram depicting a transducer attached to two exciters.

FIG. 7B is a diagram a depicting a transducer attached to four exciters.

FIGS. 9A and 9B are schematic diagrams depicting how the shortest shear wavelength can be used to determine when a shear wave direction is parallel to a plane of an ultrasound image.

DETAILED DESCRIPTION OF EXAMPLE EMBODIMENTS

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense. The specific details disclosed herein are not to be interpreted as limiting, but rather as a representative basis for teaching one skilled in the art how to employ the present invention in virtually any detailed system, structure, or manner.

The invention may be applied to image the abdomen of a person or animal although the invention can also be used to image other parts of the body. The liver is used as an illustrative example of an organ that can be imaged with this invention.

Throughout this document: "exciter" refers to a device or mechanism that has a component in contact with the patient which oscillates to shake or vibrate the tissue. An exciter may be driven by a suitable excitation signal to continuously shake or vibrate tissue during a chosen period. A "transducer" or "ultrasound transducer" is a probe that contains an array of piezo-electric crystals which can transmit high frequency sound waves and receive echoes to provide spatial information that may be applied for image reconstruction and tissue displacement tracking. "belt" is a band that can be wrapped tightly around a patient and secured in place. A belt may be secured using a hook and loop fastener (e.g. Velcro™) or other fastener. A belt may support attachments and holders for both an exciter and an ultrasound transducer.

Figure 1:
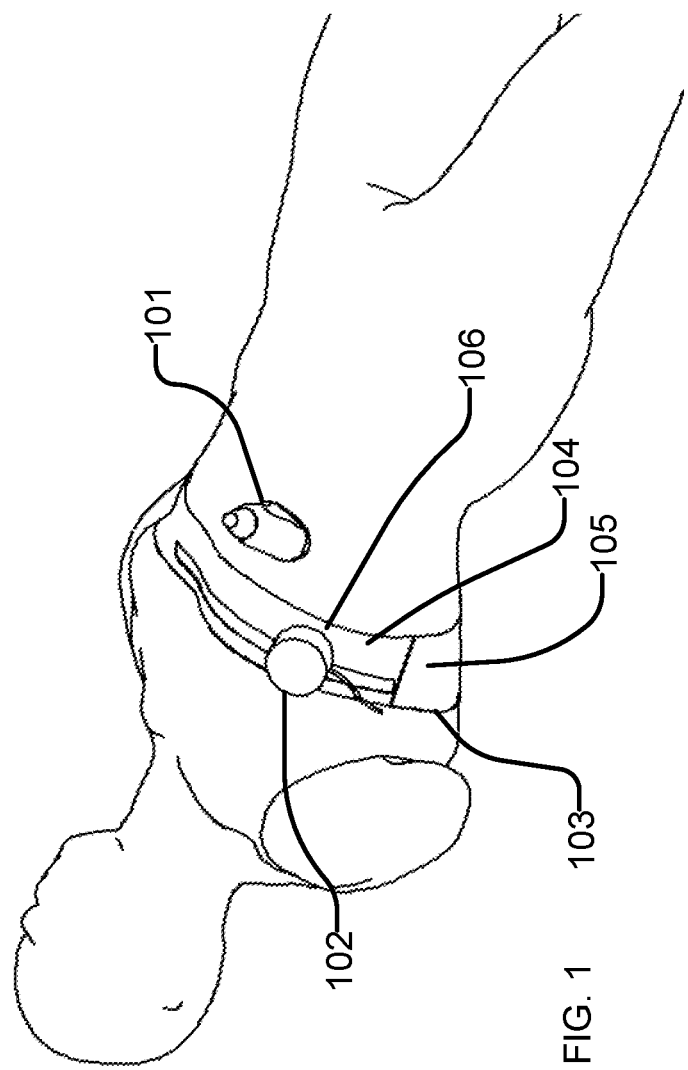
FIG. 1 is a diagram depicting a semi-rigid, semi-elastic belt used to hold an exciter in contact with a patient in an example embodiment of the invention.

FIG. 1 shows a semi-elastic, semi-rigid belt 105 that may be used to hold an excitation mechanism or 'exciter' 102. Belt 105 has a rigid part 103 that wraps around the back (posterior) of the patient to fix exciter 102 in place, on the right side of the patient. An elastic part 104 of belt 105 wraps around the front (anterior) of the patient. The elasticity of part 104 allows the patient's rib cage to expand and contract during breathing. Exciter belt 105 is used to position exciter 102 on the patient's skin in a region 106 spanning ribs 8-12 which in turn vibrate and provide a consistent excitation wave into the liver tissue. Exciter 102 is wide enough so that it is in contact with several ribs simultaneously to ensure the vibration is transmitted to the rib cage and not absorbed in the spaces in between the ribs.

In alternative embodiments, exciter 102 is mounted on a non-elastic, in some embodiments rigid, portion of belt 105. In other alternative embodiments belt 105 is elastic along all or most of its length. Belt 105 provides an anchor for one or more exciters 102. Exciter(s) 102 may be at fixed positions on belt 105 and/or may be adjustable relative to belt 105.

Figure 2:
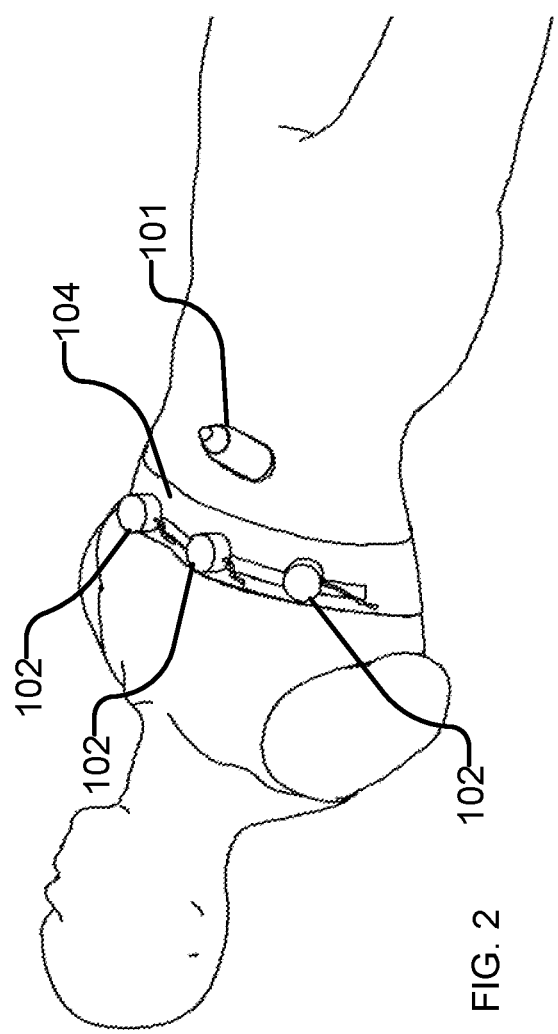
FIG. 2 is a diagram depicting several exciters placed along an exciter belt in a further example embodiment of the invention.

FIG. 2 shows another possible embodiment of the setup to provide adequate shear wave intensity. Here, multiple exciters 102 are placed along belt 105 to increase the wave propagation and coverage. This allows for stiffness measurements deeper into the tissue of the liver or other organs of the abdomen.

Figure 3A:
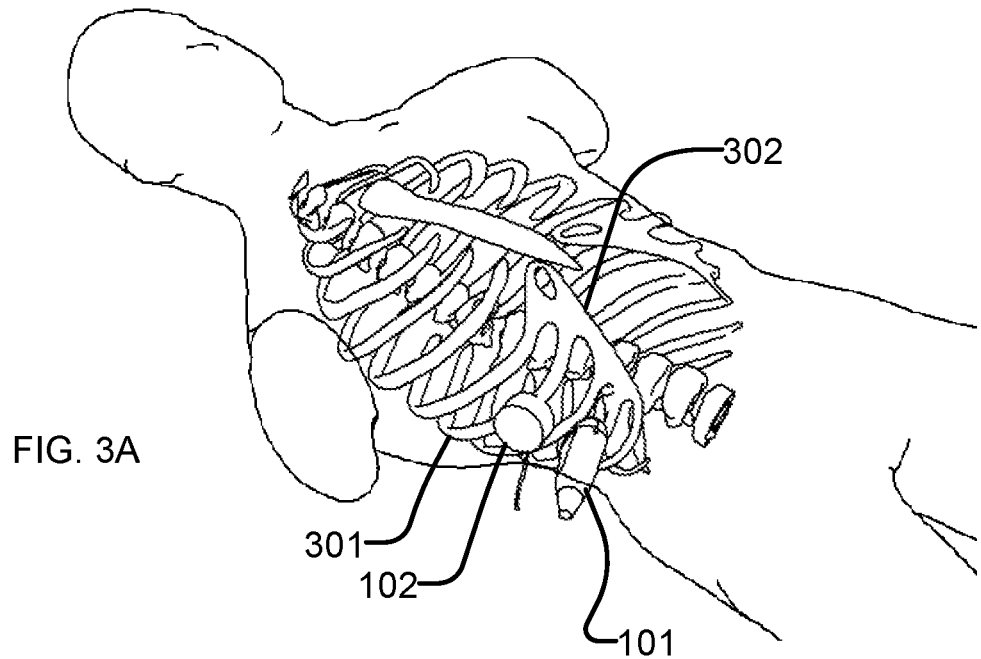
FIGS. 3A and 3B respectively show transducer placements that may be applied to image the liver from either between the ribs or under the ribcage.
Figure 3B:
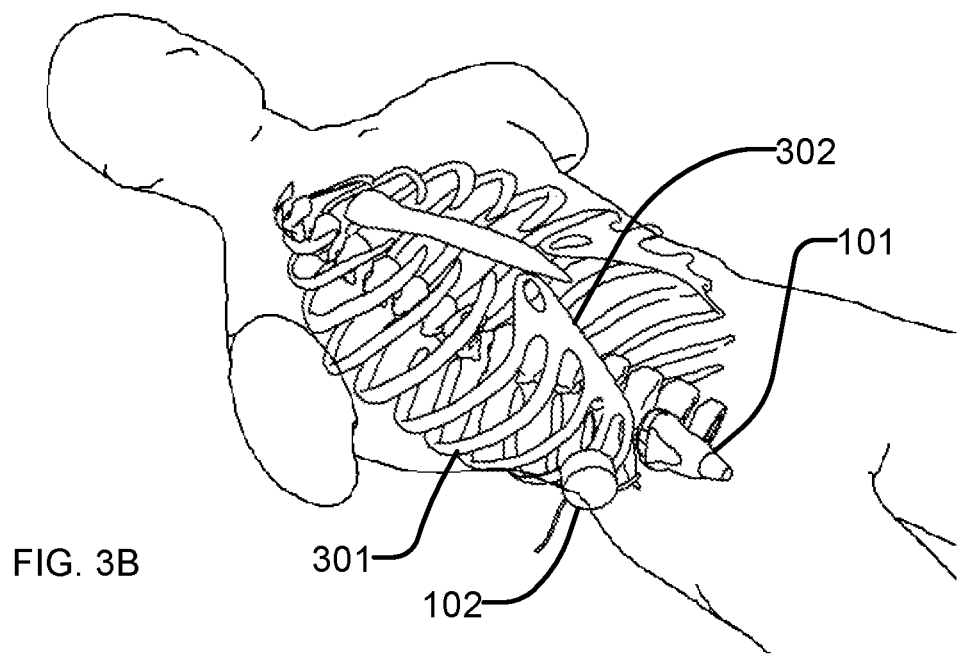

Appropriate placement of ultrasound transducer 101 facilitates imaging the liver or other abdominal organs. FIGS. 3A and 3B illustrate two different methods for viewing the liver. In FIG. 3A transducer 101 is placed in between two ribs 301 on the right hand side of the patient. Although it is not possible to obtain ultrasound images when looking at tissue through bone, it is possible to view an organ such as the liver through the softer tissue in between the ribs. As an example, the liver is located immediately inside the ribcage 302 on the right hand side so it can be viewed easily in this way. Other organs may be imaged in other fields of view available between ribs. In FIG. 3B transducer 101 is placed under (inferior to) the ribcage 302. In both of FIGS. 3A and 3B a suitable example position for an exciter 102 is also shown for reference.

Figure 4A:
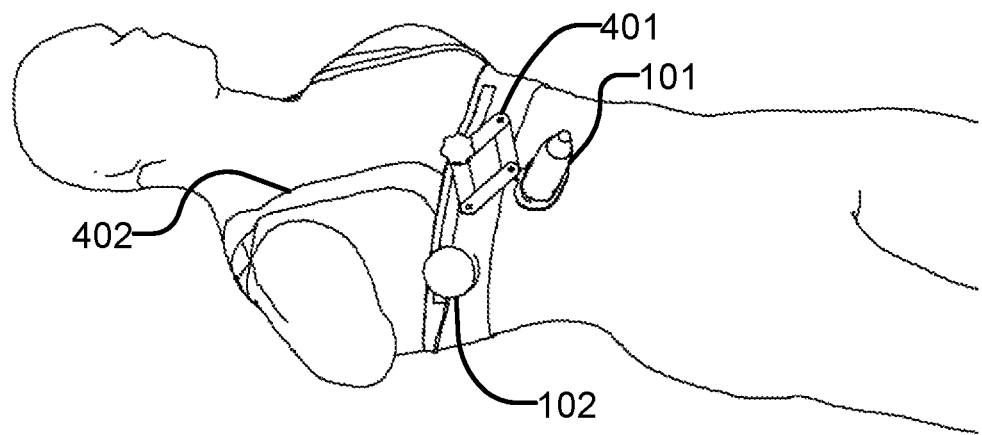
FIG. 4A is a diagram depicting example transducer support and positioning using a lockable adjustable support attached to a belt supported by shoulder straps.
Figure 4B:
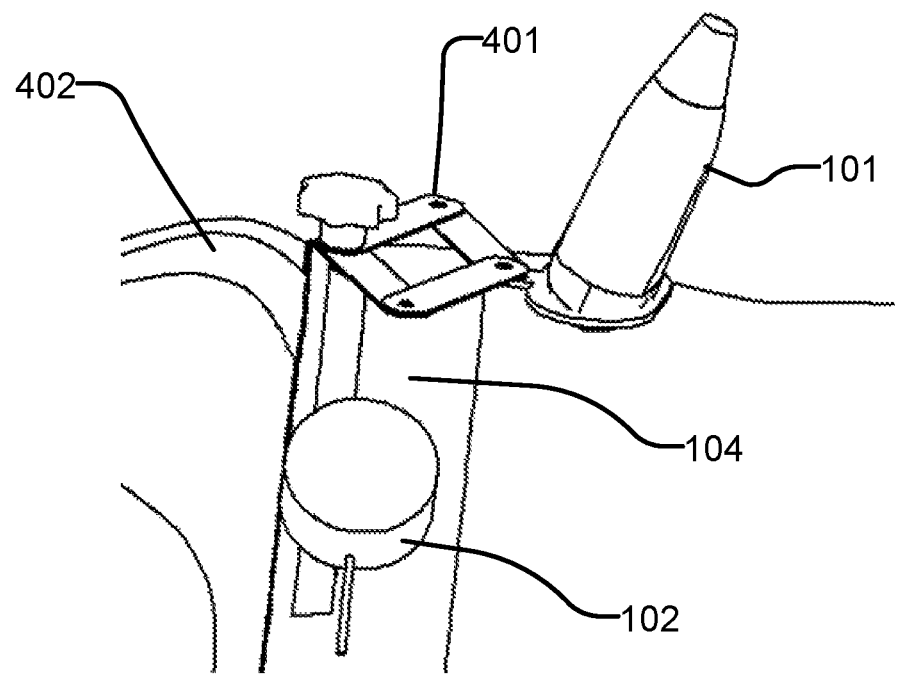
FIG. 4B is a diagram depicting the transducer support and positioning structure of FIG. 4A.

FIGS. 4A and 4B show one way to attach an ultrasound transducer 101 to an exciter belt 105. A six degree of freedom support 401 holds and positions transducer 101 to get a good image of the liver or other tissue of interest. Once transducer 101 has been positioned and rotated so that the liver can be seen, support 401 is locked to keep transducer 101 fixed. Shoulder straps 402 may be provided to constrain the motion of transducer 101 once it is locked in place.

Some embodiments acquire three-dimensional ultrasound data which can be processed to measure properties of shear waves in imaged tissues. Three-dimensional ultrasound data may, for example, be acquired by moving an ultrasound transducer so that an imaging plane sweeps out a volume. The movement may, for example, comprise tilting the ultrasound transducer relative to a transverse axis lying in or parallel to the image plane, rotating the ultrasound transducer about a longitudinal axis and/or translating the ultrasound transducer.

For example, in some embodiments three-dimensional images may be acquired by sweeping a two dimensional array through a small angle (e.g. a total angle in the range of 10 to 20 degrees). However, during such a sweep transducer 101 may move along the surface of the tissue changing the position from which the tissue is being imaged. While this change in position is normally not an issue, it makes imaging through a small window difficult, such as when imaging between the ribs 301 (see FIG. 3A).

Figure 5A:
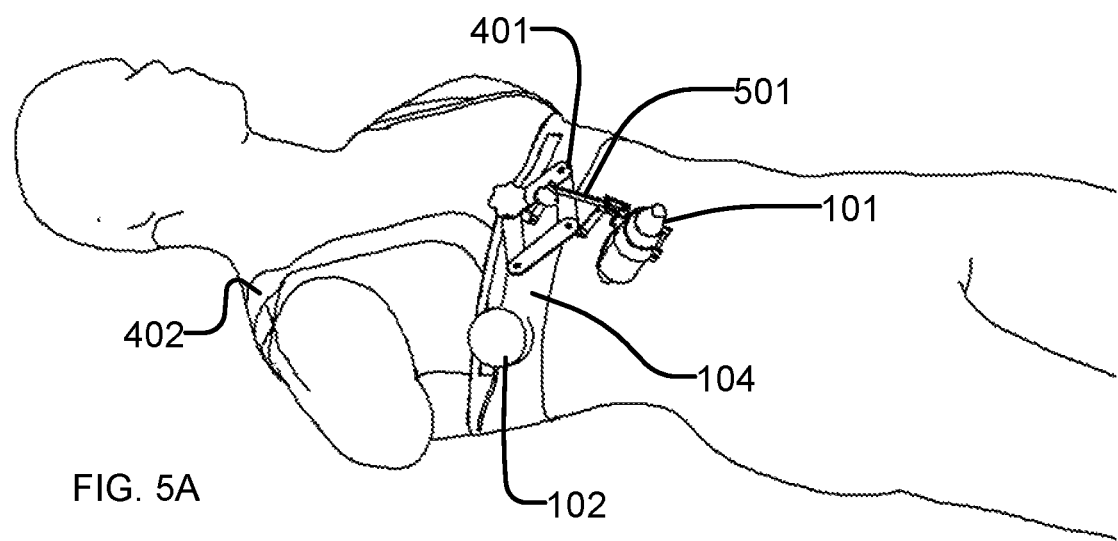
FIG. 5A is a diagram depicting a transducer support having a remote centre of rotation.
Figure 5B:
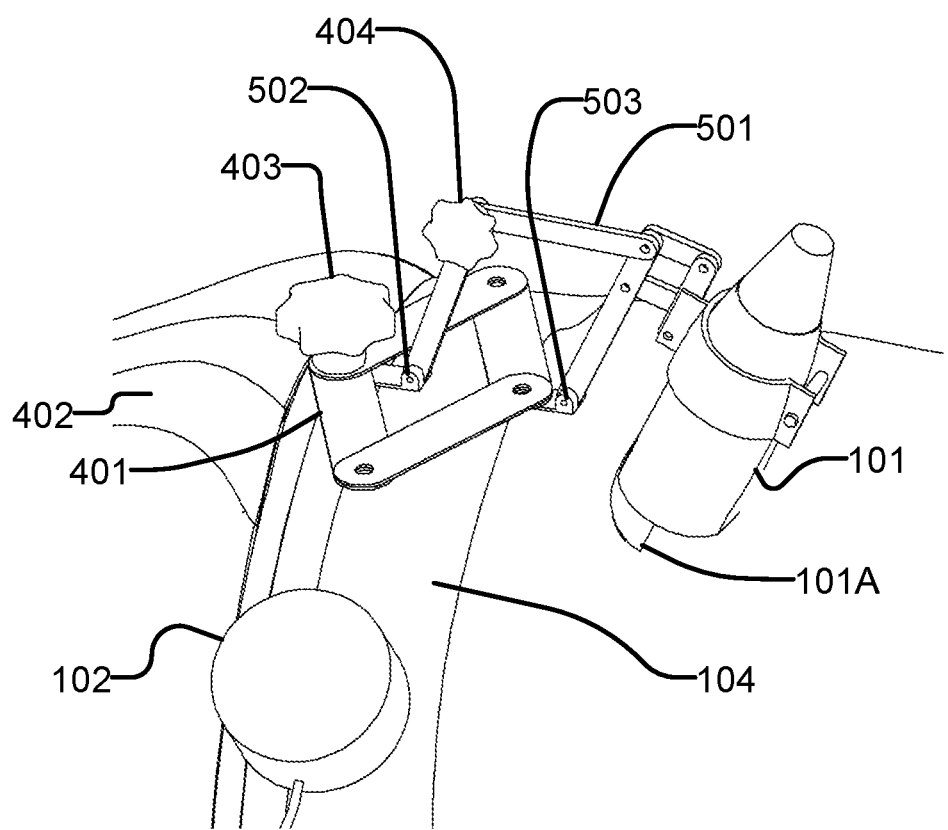
FIG. 5B is a close-up view of the transducer support of FIG. 5A.

To make imaging easier, some embodiments provide a remote centre of rotation mechanism 501 that can be used to rotate the imaging plane but keep the same point of contact on the tissue. FIGS. 5A and 5B show an example of a remote center of rotation mechanism 501. FIGS. 5A and 5B show an example embodiment in which remote centre of rotation mechanism 501 is integrated with a transducer support.

As shown in FIGS. 5A and 5B, transducer 101 is mounted on a parallelogram linkage so that an imaging array 101A stays at a given position defined by a stabilizer mechanism 401, which can be locked in place through a locking handle 403 or handles 403 and 404. The parallelogram linkage can pivot about its joints 502 and 503, allowing transducer 101 to pivot about imaging array 101A. Stabilizer mechanism 401 can be built externally to move a transducer or miniaturized and built within the transducer housing to move a transducer array (e.g. 101A) relative to a transducer housing. Stabilizer mechanism 401 may allow transducer 101 to rotate about an axis parallel to the ribs. In some embodiments the axis of rotation may be parallel to and in between two adjacent ribs. Transducer 101 may rotate about an axis that passes through the point of contact with the tissue of the patient or may rotate about an axis that passes through a point underneath the point of contact (for example 3 cm underneath the skin at the point of contact). When viewing between the ribs of a patient image data may be processed to identify and discard shadowed signals resulting from the adjacent ribs of the patient.

Stabilizer mechanism 401 may allow transducer 101 to rotate through a small angle, for example through angles in the range of 5° to 10° in each direction or a total angle of 10 to 20 degrees. In other example embodiments the transducer may be rotated through angles of less than 7° or more than 10° in one or both directions.

In some embodiments transducer 101 may rotate about a lengthwise (longitudinal) axis (e.g. an axis generally perpendicular to a surface on which the elements of imaging array 101A are located. Rotation of transducer 101 about a lengthwise axis may allow the operator to improve the alignment of the shear waves with an imaging plane of the transducer.

Figure 6:
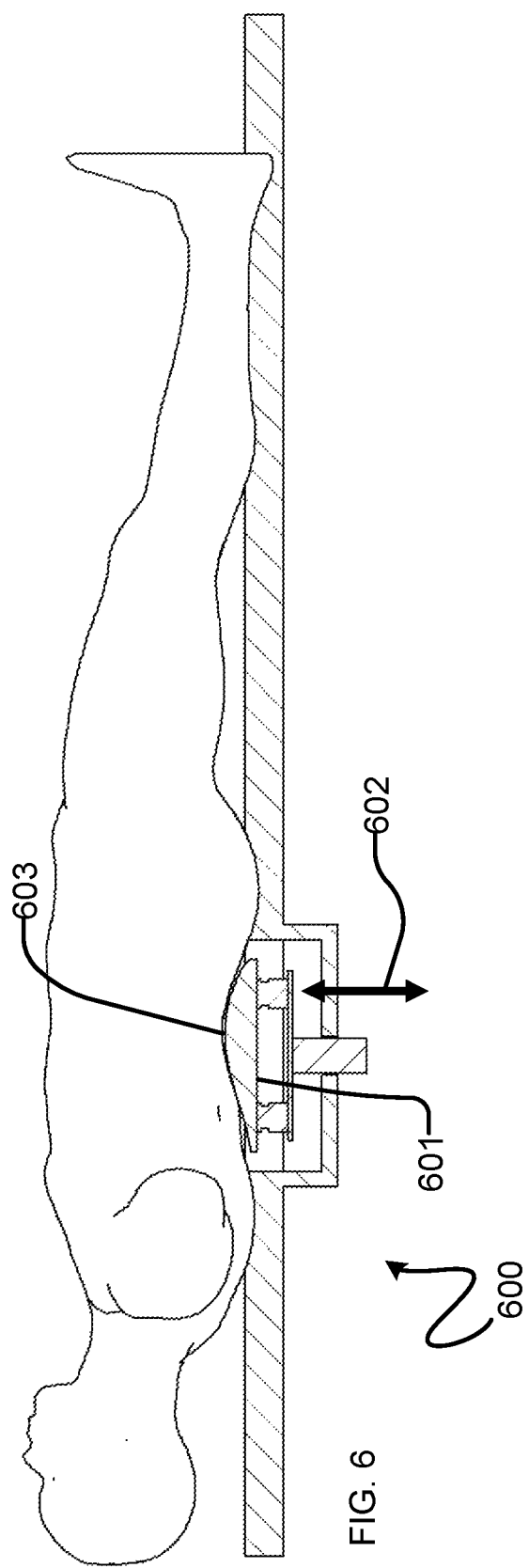
FIG. 6 is a diagram depicting an alternative exciter mechanism comprising a large flat surface that can be placed under a patient in a supine position.

FIG. 6 shows a different example apparatus that may be used for imaging the liver or other organs. In this embodiment, an exciter 600 comprising a large flat plate 601 is used to shake the tissue from below the patient who is lying in supine position. Exciter 600 is designed so that it is thin enough to be comfortably be placed under the patient's back. A mechanism may be provided for adjusting a height 602 of exciter 600. Height 602 may be adjusted to ensure good contact with patient's back 603 and shear wave transmission. In an alternative embodiment exciter 600 is housed in a recess (not shown) in a surface on which the patient is lying.

FIGS. 7A and 7B show how multiple configurations can be combined to maximize the benefits from each of the design features. Multiple exciters 102 may be attached directly to a transducer 101. Transducer 101 may optionally be placed and fixed using belt 105, shoulder straps 402 and the six degree of freedom, remote centre of rotation transducer support 401, 501. Exciters 102 may collectively span several ribs (e.g. span a distance of 7 to 15 cm). In some embodiment each exciter 102 has a large flat footprint.

Figure 8A:
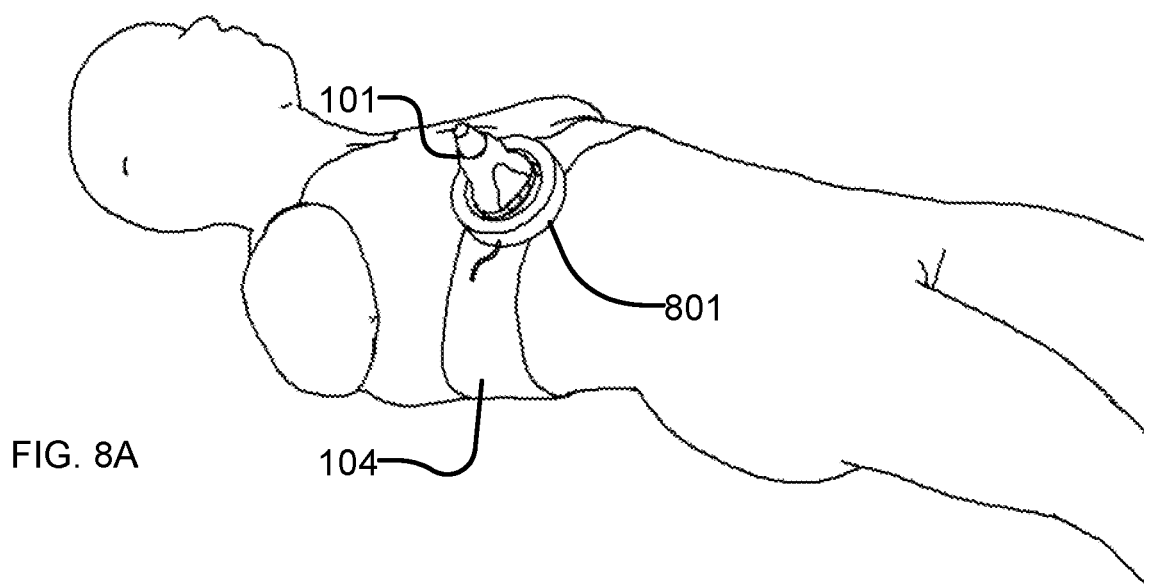
FIG. 8A depicts a transducer encircled or surrounded by an exciter which acts as a vibration source.
Figure 8B:
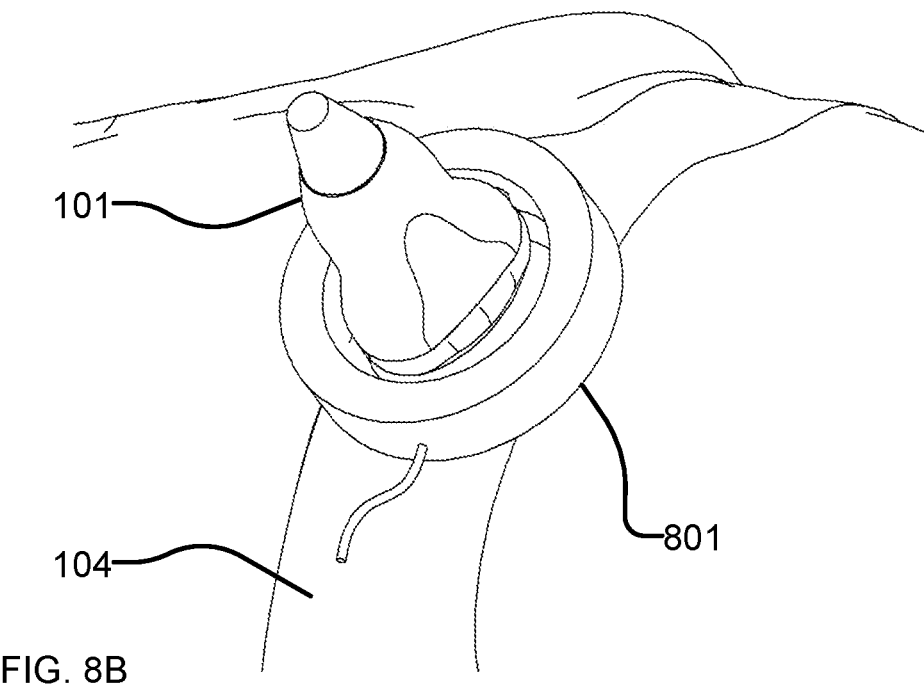
FIG. 8B is a magnified view of the transducer of FIG. 8A.

FIGS. 8A and 8B show another configuration that comprises a different exciter 801, which has a flat annulus or ring shape that completely or substantially encircles transducer 101. Exciter 801 is attached to transducer 101 which may optionally be supported using any of the mechanisms described above.

In any embodiment of the system, the excitation signal and pattern may optionally be controlled and manipulated to optimise the coverage of a tissue of interest, such as the liver by shear waves. Excitation signals may be provided by one or more exciters. Each exciter may be driven by a selected excitation signal which may comprise one or more than one frequencies. The excitation signal(s) may be manually or automatically adjusted in response to signals received by the transducer. For example, if the shear waves are too small to be accurately measured by the transducer the amplitude(s) of one or more excitation signal(s) may be increased to produce greater tissue motion.

Two or more excitation frequencies may be applied simultaneously by the same exciter or different exciters. Two or more exciters may be operated to excite a patient's tissues with different relative phases and amplitudes, in order to generate a three dimensional pattern that covers a suitably large volume. Excitation frequencies may be selected based on patient size, initial wave amplitude and direction, or automatically based on detected waves.

If 2D ultrasound is used then the operator may move the probe manually while observing the resulting ultrasound image to determine whether a three dimensional pattern of shear waves covering a suitably large volume has been obtained.

In an example embodiment, the system displays an ultrasound image of the tissue being examined and an image of the shear waves in real time. With a 2D ultrasound transducer the operator identifies a 'central' plane which is a plane through the tissue which provides substantially the largest cross-section of the tissue for a given range of motion of the transducer.

When a given shear wave pattern is generated, certain regions called nodes can appear. There is relatively little tissue motion at or near the nodes. Nodes appear in ultrasound images as regions with little movement. Without tissue motion, tissue elasticity cannot be determined accurately. The presence of such nodes in a volume of interest being imaged can lead to unreliable elasticity estimation.

Nodal regions in tissue can be defined over a pre-determined tissue region, for example, a sphere of a given diameter, for example 20 mm, having a maximum tissue motion that is below a given threshold, for example 100 microns. In some embodiments ultrasound data is processed to automatically detect such nodal regions.

In some embodiments signals driving one or more exciters are controlled to avoid nodes within a volume of interest and/or to cause nodes to move from one part of a region of interest to another, thereby allowing measurement of tissue elasticity throughout the region of interest. This may be done manually or automatically.

In some embodiments the signal(s) driving one or more exciters are controlled by vibration control software. The vibration control software may, for example control the phase and/or frequency and/or amplitude of one or more signals so as to cause any nodes to move from one location to another. This can enable elastography imaging of an entire region of tissue.

The frequency of vibration of one or more exciters can be adjusted until a nodal region found at a specific location in tissue is eliminated. The frequency may be adjusted by picking a series of frequencies, or may be adjusted automatically based on a feedback loop using sequential or consecutive measurements.

In an example embodiment data is collected for excitation at frequencies of 45 Hz, 50 Hz, 55 Hz and 60 Hz. Generally, data may be collected for excitation at 1, 2, 3, 4 or more frequencies. For deeper abdominal imaging, it is generally the case that the frequencies are in or near the 50 Hz to 60 Hz range. These frequencies may be adjusted based on the characteristics of the patient, such as the size of the patient and/or the size or configuration of an organ being imaged (e.g. the patient's liver). For smaller patients frequencies up to and potentially higher than 70 Hz may be suitable. For larger patients, frequencies as low as, or lower than, 45 Hz may be suitable. Alternatively, the relative phase of two or more exciters may be adjusted until a nodal region at a specific location of tissue is eliminated or moved sufficiently to obtain a measure of elasticity at the specific location of tissue.

The direction of shear waves resulting from excitation by one or more exciters may be adjusted by changing the frequencies and/or phases of excitation signals which drive the exciters. The most accurate elasticity estimation can be made when the tissue motion associated with a shear wave is in the same plane as the imaging plane. Ultrasound-based measurements of tissue motion may have significantly better precision where the tissue is motion is parallel to the ultrasound propagation than when the tissue motion is non-aligned with the ultrasound direction of propagation. In some cases the resolution may be improved by an order of magnitude by alignment of the direction of tissue motion under the influence of shear waves with the direction of ultrasound propagation.

FIGS. 9A and 9B illustrate an example shear wave 902 and its direction 901 which can be controlled by changing the relative phases of the excitation signals driving exciters 102. The perceived wavelength 904+905 as seen in the ultrasound imaging plane 903 is shown to be the shortest 905 when the shear wave direction is parallel to the ultrasound imaging plane. For a 3D transducer, the ultrasound imaging plane 903 is interpreted as the central plane of the imaging volume. Without knowing a priori the direction of the shear wave 901, in order to align (if possible) the transducer axis 903 with the wave direction 901, a system that measures tissue motion only along a line or in a plane will tend to overestimate tissue stiffness because its measurement provides a wavelength longer than the actual wavelength of shear waves.

Shear waves delivered by a system of exciters 102 may be controlled to be parallel to the imaging plane in a given region of interest by varying the direction of the shear waves until the shortest shear wavelength is achieved. In some cases, this may be done separately for different portions of a volume of interest.

In some circumstances it may be desired to manually adjust the direction of propagation of shear waves, either by repositioning one or more exciters or by modifying the frequencies and/or phases of excitation signals of one or more exciters so as to optimize the wave propagation for a given patient. For example, in some obese patients it may be desired to have shear waves propagate through the body in a modified direction.

The direction of the shear waves may be controlled automatically using a closed feedback loop based on sequences of measurements. For example, ultrasound data may be processed to determine a wavelength of shear waves in imaged tissues and parameters of excitation signals (e.g. frequencies, phases and/or amplitudes may be varied until a minimum of the measured wavelength has been achieved). Systematic searches for a minimum may use a sampling of the phases, frequencies and amplitudes at regular intervals or along local gradients estimated from small changes in these phases, frequencies and amplitudes.

In some embodiments an exciter or several exciters may be attached directly to the transducer (see FIGS. 7A and 7B) so that the shear waves propagate directly away from the transducer face. An operator may adjust the imaging plane by moving the transducer to align the imaging plane with the direction of greatest tissue motion.

Lower excitation frequencies provide deeper penetration and increased tissue displacement amplitude. The trade-off is that at lower frequencies the resolutions of resulting elasticity images are lower. Measurement of the elasticity of the tissue may provide higher resolutions at higher excitation frequencies as the wavelengths are shorter and more periods of the shear wave may be measured per unit distance at higher excitation frequencies. The maximum frequency component for a given patient may be found by adjusting the excitation frequency and measuring the amplitude of the tissue displacement to verify that the signal to noise ratio is reasonable.

A cross correlation method may be used to determine the signal-to-noise ratio. Corresponding patches of ultrasound images taken at spaced apart times may be compared by cross correlation to measure tissue motion. A correlation of 1.0 means that the ultrasound images are undeformed, and merely shifted due to shear wave motion. A low correlation indicates that the images differ significantly, for example as a result of noise or deformation. A reasonable signal-to-noise ratio has been found to be met where the correlation is greater than 0.9.

Another signal-to-noise measure can be determined from the fit of displacement measurements obtained at spaced apart times to a phasor (amplitude and phase) fitting process that gauges how closely the displacement measurements resemble a pure sinusoidal waveform at the frequency of the excitation. A perfect fit gives an error of zero meaning that the samples trace out a perfect sinusoid. By this method it is assumed that the time domain displacement is the actual displacement signal. The error between the measured displacement and the fitting cosine is then the noise and the ratio of the RMS of the signal to the RMS of the estimated noise is a measure of the signal-to-noise ratio.

FIGS. 10A through 10D present an advantageous configuration that is similar to FIG. 6. This configuration allows the medical professional taking a liver measurement to maneuver ultrasound transducer 101 in a manner that is similar to conventional ultrasonography of the liver, while at the same time benefiting from a strong field of shear waves through the liver and throughout the abdomen. Without repositioning exciter 102 or interference from it on the patient 610, transducer 101 can be placed in position 640 to image the liver between the patient's ribs, or in position 641, to image the patient's liver trans-abdominally.

Patient 610, shown along the craniocaudal axis in FIG. 10, lies on top of an exciter board 611 placed on the bed mattress 612. Board 611 is placed under the patient's back 603 and is similar to that presented in FIG. 6. Board dimensions that have been tested and fit most patients are between 40 and 60 cm axially (left right direction of the patient) and 10 to 20 cm wide (superior-inferior direction of the patient). A stiff light board is beneficial. For example, board 611 may comprise a structure comprising a honeycomb core reinforced on either face with sheets of a fiber reinforced plastic material such as Kevlar™ or carbon fiber. Exciter board 611 may be fitted with a resilient layer (not shown) that allows for increased amplitude of vibration.

In one embodiment, exciter 102 actuating motion of board 611 is inertial and generates forces by moving a counterweight linearly or rotationally.

In one embodiment (FIGS. 10A, 10B, 10D), the forces generated by exciter 102 are in the vertical direction, generating forces 616, 617 through a rocking motion of board 611 that acts on the patient's back.

Figure 10A:
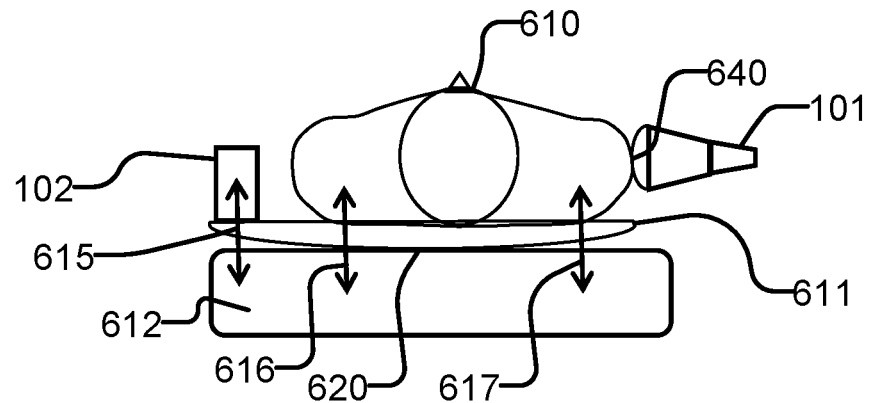
FIG. 10A is a diagram depicting a patient on an exciter board according to an embodiment of the invention.
Figure 10B:
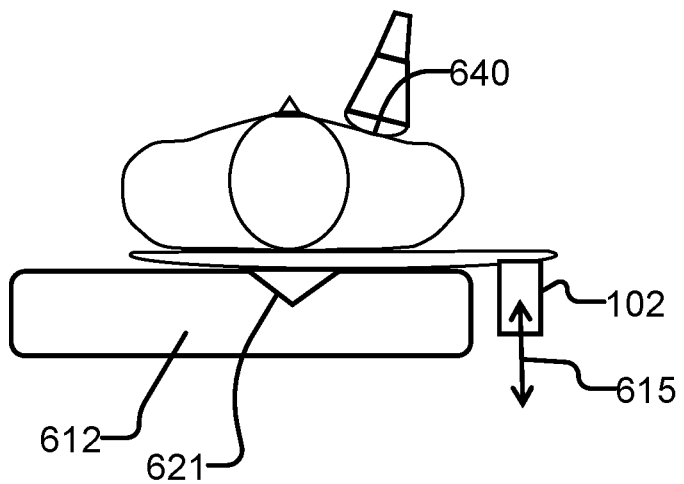
FIG. 10B is a diagram depicting a patient on an exciter board in which an exciter is attached below the exciter board.
Figure 10C:
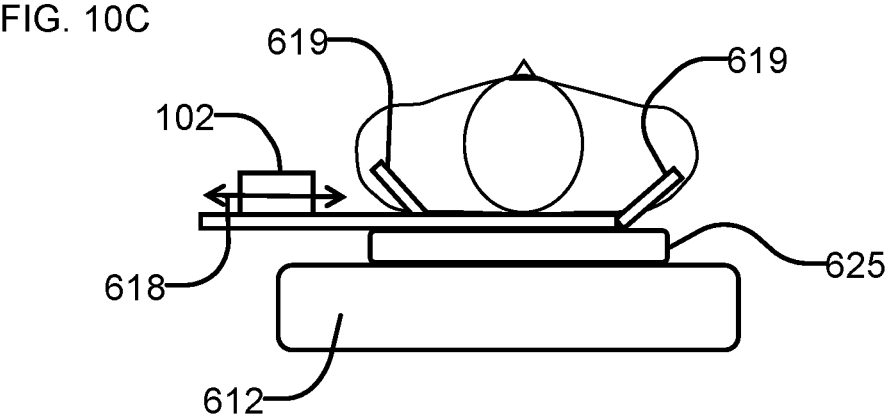
FIG. 10C is a diagram depicting a patient on an exciter board in which an exciter generates forces in a horizontal direction and couplers transmit force to the ribs.
Figure 10D:
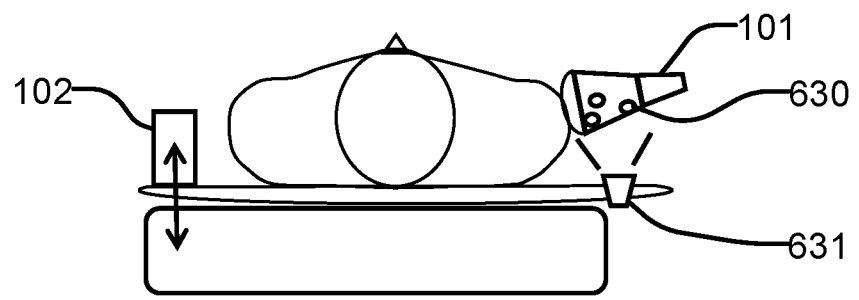
FIG. 10D is a diagram depicting a patient on an exciter board in which a camera attached to the exciter board tracks a transducer.
Figure 11:
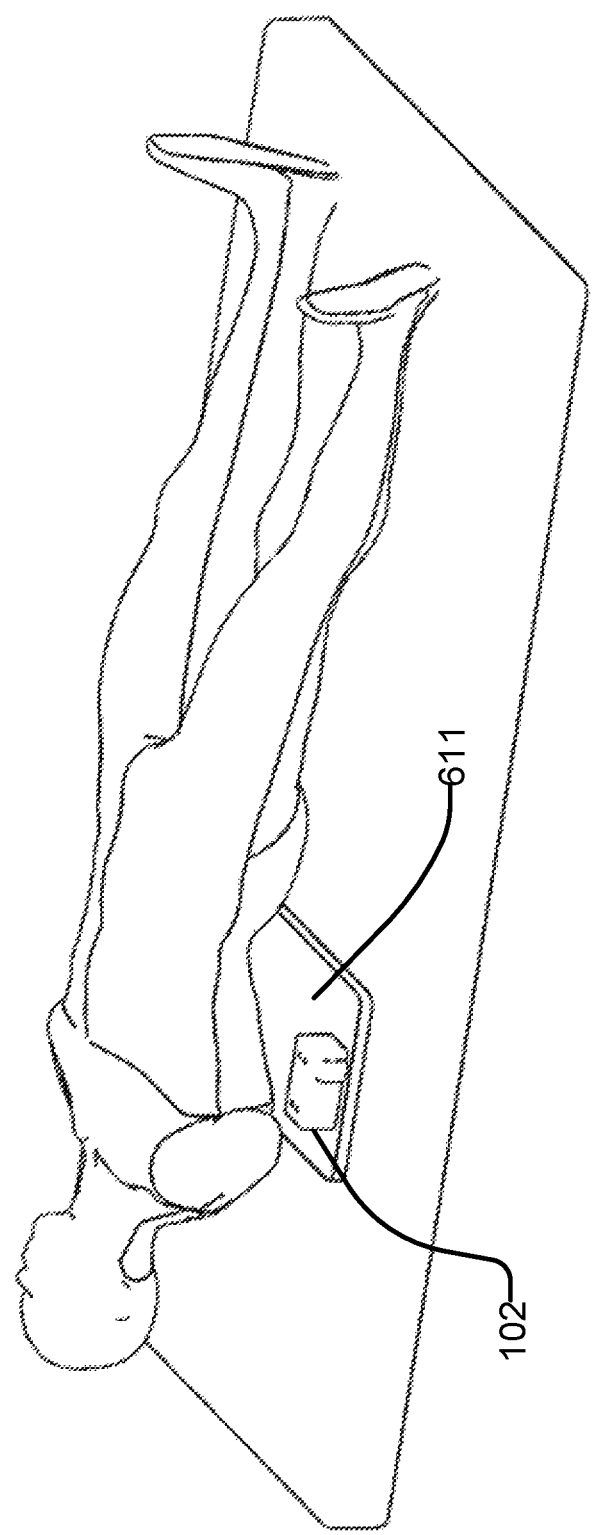
FIG. 11 is a diagram showing a patient lying on an external vibrator comprising a top-mounted exciter.

In some embodiments (e.g. FIG. 10O), the forces generated by exciter 102 are horizontal (in the plane of board 611). The forces may, for example, be directed in the lateral left-right direction of the patient, with motion being imparted to the patient through couplers 619 (straight or curvilinear) that push against the patient's ribs. Couplers 619 may, for example, comprise adjustable bolsters or supports that project on the top side of board 611 and may be brought against the sides of a patient's ribcage while the patient is lying on board 611. In some embodiments at least one coupler 619 is removable to facilitate sliding board 611 under a patient who is already lying down.

Where the ultrasound transducer is anterior for transabdominal imaging the arrangement of FIG. 10C may allow for the highest amplitude of tissue motion to occur in the region of highest attenuation of ultrasound images and allow for the lowest attenuation of ultrasound to occur where the shear waves are more attenuated. This combination of factors may facilitate accurate tissue motion measurements throughout the imaging plane.

In some embodiments the forces generated by exciter 102 are oriented in a diagonal direction. A diagonal force may be imparted by a set of exciters 102 each applying either horizontal or vertical forces, or by one or more exciters each imparting force diagonally.

In further embodiments, the forces generated by one or more exciters may change in direction. The direction of applied forces may be altered, for example by changing the phase difference between two exciters, e.g. one exciter 102 generating horizontal forces as shown in FIG. 10O, with a second exciter 102 generating vertical forces as illustrated in FIG. 10B. For example. Such phase changes may be applied to cause the direction of net forces applied to board 611 to rotate or shift. As another example, rotating forces may be generated by an unbalanced rotary motion. For example, an exciter may comprise an unbalanced rotor driven to rotate at a desired frequency.

The motion of the ribs may limit or modify the motion of any tissue within the patient's ribcage. The amplitude, phase, frequency or direction of propagation of shear waves produced by each of one or more exciters may be modified to affect the tissue motion within the ribcage. In some embodiments the position of the exciters and/or the transducer may be adjusted to account for the geometry and flexion directions of the ribs.

In some embodiments, exciter board 611 is placed on a support that facilitates movements of board 611 in the plane of board 611. For example, board 611 may be supported by one or more of: a pillow (or set of pillows) 625, one or more inflatable cushions, one or more springs etc. Supporting board 611 in a way that allows board 611 to be moved relatively easily facilitates delivery of shear waves of greater amplitude into the tissues of a patient lying on board 611.

In some embodiments pillows may be inflatable pillows to accommodate patients of various sizes while providing spring-like characteristics to the bed. In other embodiments the pillows may be hospital pillows. In yet other embodiments a combined exciter and pillow may be provided. A combined exciter and pillow may allow that the resulting vibrations are substantially independent of the bed, mattress and patient body habitus.

Board 611 may have various configurations. For example, board 611 may be formed with a curvature 620 to make it easier to rock the patient along the craniocaudal axis; or, depending on the thickness and stiffness of the mattress 612, board 611 may comprise a fulcrum or keel 621, penetrating into the mattress 612, as shown in FIG. 10B, again to facilitate rocking the patient's back to generate shear waves in the abdomen.

Exciter(s) 102 may be placed in any suitable locations. For example, exciter(s) 102 may be located on one or both sides of a patient (e.g. left and/or right side of the patient as shown in FIGS. 10A and 10B. Exciter(s) 102 may be mounted above board 611 (e.g. as in FIG. 10A), below board 611 (e.g. as in FIG. 10B) or in a cutout in board 611 (not shown). Exciter(s) 102 may be mounted above a top surface of a mattress (e.g. as in FIG. 10A) or to one side of the mattress surface (e.g. as in FIG. 10B).

Exciter board 611 may house additional sensors, such as accelerometers, to quantify the acceleration or velocity or displacement underneath the patient's liver, or a camera 631, that may be used to localize an ultrasound transducer 101 by tracking a target 630 affixed to the transducer.

As described above, the excitation frequencies used, along with their relative phases and amplitudes, may be controlled to: remove low displacement nodes, ensure the shear wave direction is parallel to the imaging plane and/or to ensure adequate overall displacement in a given region of interest. A pre-set excitation signal can be generated taking into consideration all of these criteria to produce the most reliable configuration for the majority of situations. For any given exciter the sum of different frequencies of the pre-set signal should not be so high as to saturate the amplifier of the exciter.

For smaller patients a pre-set signal may use higher frequencies then might be used for a larger patient. Higher frequencies attenuate more quickly in tissue and may be most easily used where the depth of observation is shallow. An example set of frequencies for a smaller patient is 55 Hz, 60 Hz and 65 Hz, as compared to an example set of 45 Hz, 50 Hz and 55 Hz for a larger patient.

In some embodiments where an exciter is farther from the transducer that exciter may use a lower set of frequencies and/or a higher amplitude of wave. For obese patients and patients with close-together ribs a remote center of rotation may be used as shown in FIGS. 4A and 4B to allow the transducer to effectively aim between ribs.

In some embodiments a quality measure of the tissue displacement and/or a measurement the shear wavelength in the ultrasound plane is computed in real-time and used to adjust the excitation signal in order to eliminate low displacement nodes and/or optimize the shear wave direction and amplitude. A gradient or other type of search can be used to perform this optimization. In this way, the input excitation signal can then be set for a specific patient in real time using a control loop to get the most accurate results.

Two examples of a quality measure include either of the measurements of signal-to-noise ratios described previously. A further quality measure can be established by setting minimum and maximum thresholds on the phasor magnitude. If the magnitude of the measured phasor falls below the minimum threshold then this may indicate the presence of a node or that the shear waves have not penetrated sufficiently deep into the tissue. Additionally, very high amplitudes may indicate that the tissue is undergoing large strains and may be operating in a non-linear stress-strain relation, which is undesirable. Another quality measure may be calculated by applying a window function around each point and then transferring the data to the frequency domain and looking at the spatial frequency contact of the signal which should be mostly within the range corresponding to an expected elasticity range.

A further quality measure may be the error of the fitting model used to fit onto the data spatially to find the elasticity. Fitting models suitable for this application are described in U.S. Pat. Application No 2012/000779 referred to above. For example the model can be a FEM model of the wave equation also with a constraint on elasticity range. Once an area with good waves is detected the next attempt should be to control the wave pattern to get the smallest wavelength in the imaging plane. In one implementation of this method the operator may work with each individual exciter and sweep over pre-set frequencies and amplitude steps to find which ones produce good waves in the ROI. Then the operator may select among these frequencies and amplitudes whichever one produces minimum elasticity.

In some embodiments the ultrasound transducer and the one or more exciters may be synchronized. In some embodiments synchronization of the transducer and exciters may be obtained using the internal clocks of the exciters and transducer. In some embodiments the exciters and transducer are triggered together to be phase locked.

Some embodiments provide a hardware controller that is configured by construction and/or software to perform methods that do one or more of:
  optimize the direction of shear waves (e.g. to align with an ultrasound imaging plane);
  control a field of shear waves to cause nodes to be eliminated or to move;
  optimize the frequency of shear waves for an imaging task (e.g. to obtain a good balance between imaging depth and resolution);
  optimize the amplitude of shear waves for a particular imaging application.

The controller may be connected to deliver driving signals to one or more exciters to achieve these ends. The driving signals may be controlled in response to feedback received by way of an imaging system (e.g. an ultrasound imaging system) and/or one or more additional sensors. This may be a closed loop system in which the quality measures are used to control the exciter. An example of one or more additional sensors is one or more accelerometers attached to one or more points on the patient's body and/or on a board or other patient-contacting surface by way of which vibration is delivered to the patient's body. The controller may be configured to process images from an imaging system (which is optionally integrated with the controller) to generate images. The images may include conventional images (e.g. B-mode ultrasound images). The controller may be configured to generate elastography images. The elastography images may indicate areas in which imaged tissues has different mechanical properties (e.g. stiffness, Young's modulus, and/or viscosity) by different colours. Some embodiments provide one or more displays in which B-mode and elastography images may be displayed concurrently.

In an example embodiment, the controller is connected to drive a plurality of exciters 102. The controller is configured to optimize shear wave direction in a target volume of tissue to be imaged by monitoring images of the target volume to determine an apparent wavelength of the shear waves. This may be done by processing the images to compare the positions of features in a sequence of images of the target volume. Phases of the driving signals delivered to different ones of the exciters 102 may be varied according to an algorithm or search pattern until the determined apparent wavelength is minimized. In an embodiment, an apparent wavelength is measured and the phase is adjusted to maximize the averaged sensed displacement (phasor amplitude variation) in the direction of the transducer, as this will improve the quality measure of shear wave measurement. In another example, the measured average shear wave wavelength along the direction of the transducer is used as a cost function. The phases of the arrays may then be adjusted to minimize the cost function. An optimization algorithm such as a steepest descent, among other methods, may be used to minimize the shear wave wavelength along the direction of the transducer.

In another example embodiment the controller is configured to process a sequence of images (e.g. ultrasound images of the target volume) to identify any regions of very small tissue displacements under the influence of shear waves from one or more exciters 102. If such regions are found the controller may automatically adjust the frequency(ies) and/or phases and/or amplitudes of the driving signals being delivered to one or more exciters 102 to determine if a set of frequency(ies) and/or phases and/or amplitudes of the driving signals can be found in which the possible nodes are gone or moved to another location.

Optionally such adjustment is done only for areas which satisfy a condition. The controller may identify areas within which tissue displacements are lower than a threshold and perform adjustments as above if the regions are larger than some threshold size.

In some embodiments a controller may be configured to acquire sets of data for two or more different sets of frequency(ies) and/or phases and/or amplitudes of the driving signals, process images acquired using each of these sets of driving signals to obtain a set of elastography image data for the target area, perform an assessment of the reliability of the elastography image data as a function of position in each of the resulting sets of elastography image data (this may be based on measured tissue displacements, for example) and then use reliability data resulting from the assessments to guide assembly of a composite elastography image of the target area using the most reliable data (and/or excluding the least reliable elastography data) in each part of the composite image.

In an embodiment measurements are made at two or more excitation frequencies and results of the measurements are combined (e.g. by averaging or weighted averaging). In a further embodiment the measurements are combined using a weighted average in which one or more weights are based on one or more quality measures (any of the quality measures described herein, for example).

Where data is acquired using two or more sets of excitation parameters, weights used to combine results calculated from the data obtained using each set of excitation parameters may be determined based on a comparison of the results obtained for each set of excitation parameters. Results based on the data set for which the results are most consistent may be weighted more heavily than results based on other data sets. In a still further embodiment a weighting may be determined by variability of the measurements within a region of interest. This may be useful in examining liver tissue because liver tissue may be expected to have a mostly homogenous elasticity map except near blood vessels and boundaries like the diaphragm.

Figure 12:
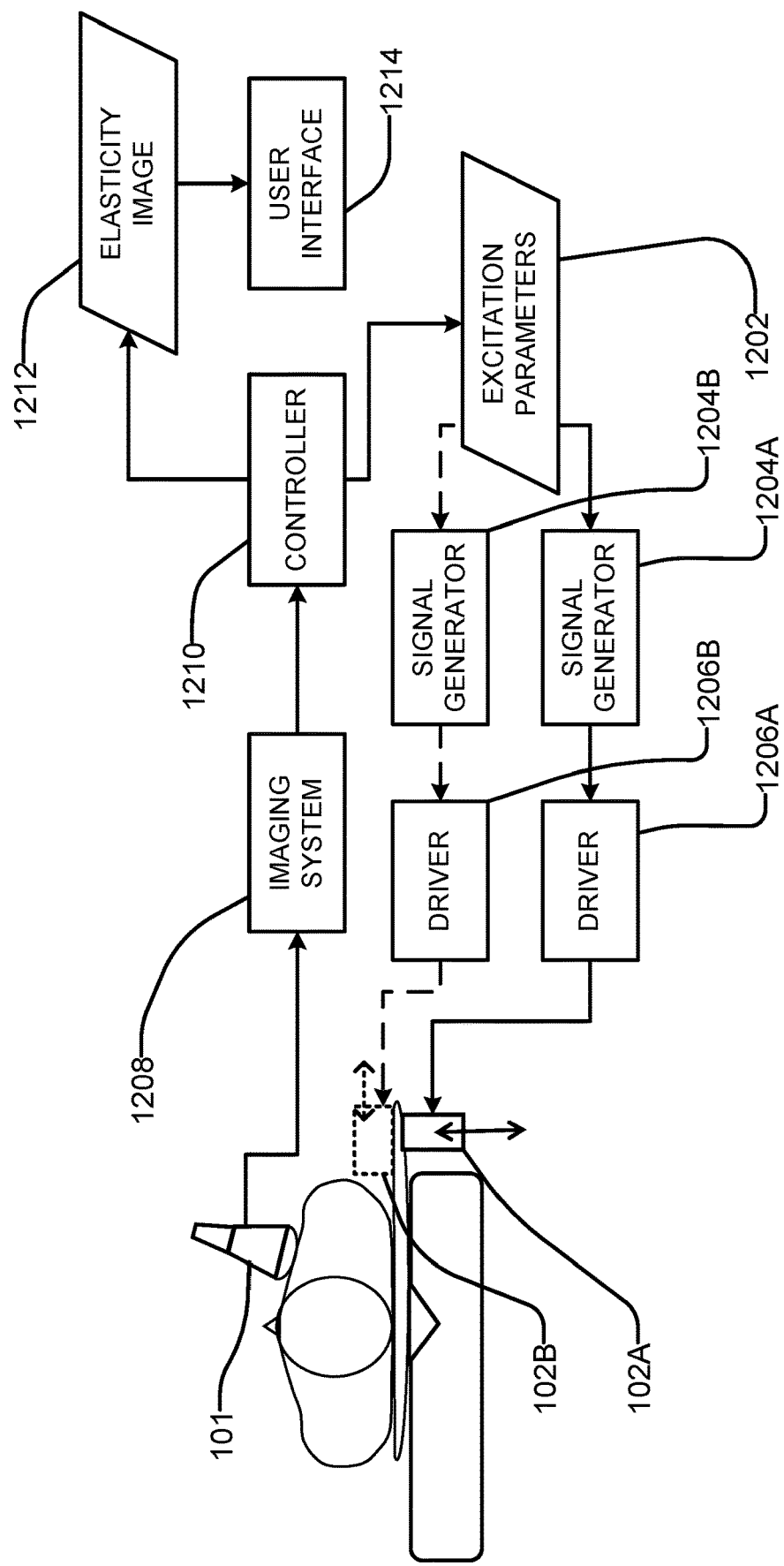
FIG. 12 is a high level block diagram illustrating an example embodiment of the invention.

FIG. 12 illustrates the operation of an ultrasound imaging system according to an example embodiment of the invention. Excitation parameters 1202 are provided to signal generators 1204A and 1204B. Signal generators 1204A and 1204B respectively deliver signals to drivers 1206A and 1206B which respectively drive exciters 102A and 102B. While two sets of signal generators, drivers and exciters are shown there may be one of each or more than two of each in different embodiments. In some embodiments the number of exciters may be different from the number of drivers or the number of signal generators.

In some embodiments Signal generators 1204A and 1206B are configured to produce digital signals which may be used by drivers 1206A and 1206B to determine any one or more of frequency, phase or amplitude to drive the exciters. Drivers 1206A and 1206B may comprise digital-to-analog converters. Initial parameters 1202 may include sets of one or more frequencies, phases, amplitudes and directions of vibration per exciter.

Exciters 102A and 102B produce shear waves in the patient's tissue. Tissue movement produced by the shear waves is observed by transducer 101. Transducer 101 outputs ultrasound echo data to imaging system 1208 which provides imaging system data to controller 1210. In some embodiments imaging system 1208 is integral with controller 1210. Controller 1210 may be configured to process images from imaging system to generate elasticity images 1212. In some embodiments, elasticity images 1212 and/or ultrasound imaging data are produced in real time on user interface 1214.

Controller 1210 may also be configured to apply any of various quality measures to the generated elasticity images and/or the data on which the elasticity images are based. In various circumstances, controller 1210 may execute a routine which modifies the excitation parameters 1202 provided to signal generators 1204A and 1204B in order to improve the quality measures in all or part of a volume of interest.

Figure 13:
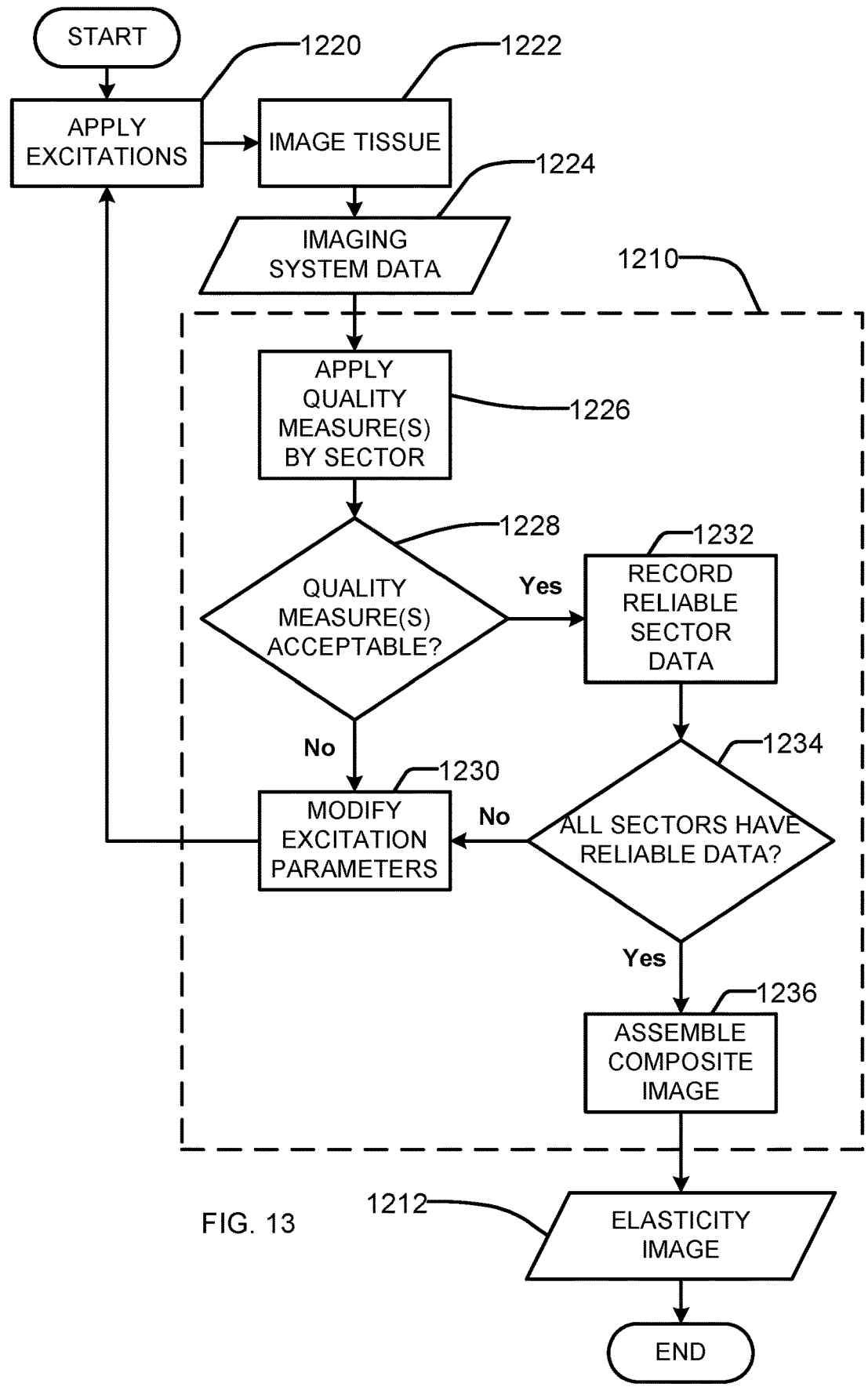
FIG. 13 is a high level flow diagram for a method that may be performed by the controller of FIG. 12.

FIG. 13 illustrates a system of operation of controller 1210 of FIG. 12 according to an embodiment of the invention. Exciters (not shown) apply excitations 1220 to a patient's tissue. Transducers (not shown) image tissue 1222 and produce imaging system data 1224. Controller 1210 applies one or more quality measures by sector 1226 and determines whether the quality measurement(s) are acceptable 1228. If the quality measurement(s) are not acceptable the controller modifies excitation parameters 1230 which are then applied to drive the exciters (not shown). If controller 1210 determines that quality measures indicate that the data for at least one sector of the image is reliable, then controller 1210 records the reliable sector data 1232. If controller 1210 determines that reliable data has been obtained for all sectors in a volume of interest then controller 1210 may assemble a composite image 1236 from the recorded sector data. If reliable data has not been obtained for all sectors the controller may further modify the excitation parameters 1230.

The assembled composite image is output as an elasticity image 1212 which may be stored and/or sent for display to a user interface (see FIG. 12). Assembling the composite image 1236 may involve applying corrections to the elasticity data or ultrasound imaging data to account for differences in excitation parameters. For example, a frequency and/or amplitude correction may be applied to account for differences in calculated tissue stiffness resulting from differences in the excitation frequency and/or amplitude between sectors. In some embodiments imaging system data 1224 and/or elasticity images may be sent in real time to the user interface. Sectors may mean a subset of lines, or a certain depth range of a subset of lines of the ultrasound image, or another suitable chosen region of interest in the ultrasound image.

When recording sector data, data for some or all sectors may be obtained using plural sets of excitation parameters (e.g. data for one or more sectors may be obtained using two, three or more different excitation frequencies). In cases where plural sets of data have been recorded for a given sector controller 1210 may use all of the sets of data or a subset of the sets of data for that sector. In some embodiments, for each sector a single set of data is chosen based on whichever excitation parameters provided the best quality measure for the imaging data of that sector. Where plural sets of data for a given sector are used controller 1210 may optionally calculate tissue properties based on each of the plural data sets and combine the results (e.g. by averaging or weighted averaging).

In some embodiments measurements are taken over a range of practical values of amplitude, frequency and phase of the exciters while monitoring quality measures based on the acquired ultrasound echo data. The quality measures may be computed in real time. The quality measures may be processed to determine the optimal set of amplitude, frequency and/or phase for each exciter that yields the best results as determined from the quality measures. In some embodiments, trends in the quality measures are used to guide a selection of amplitude, frequency and/or phase to try next. The optimal set of excitation parameters may then be applied to acquire data which is processed to yield an elastography image.

Figure 14:
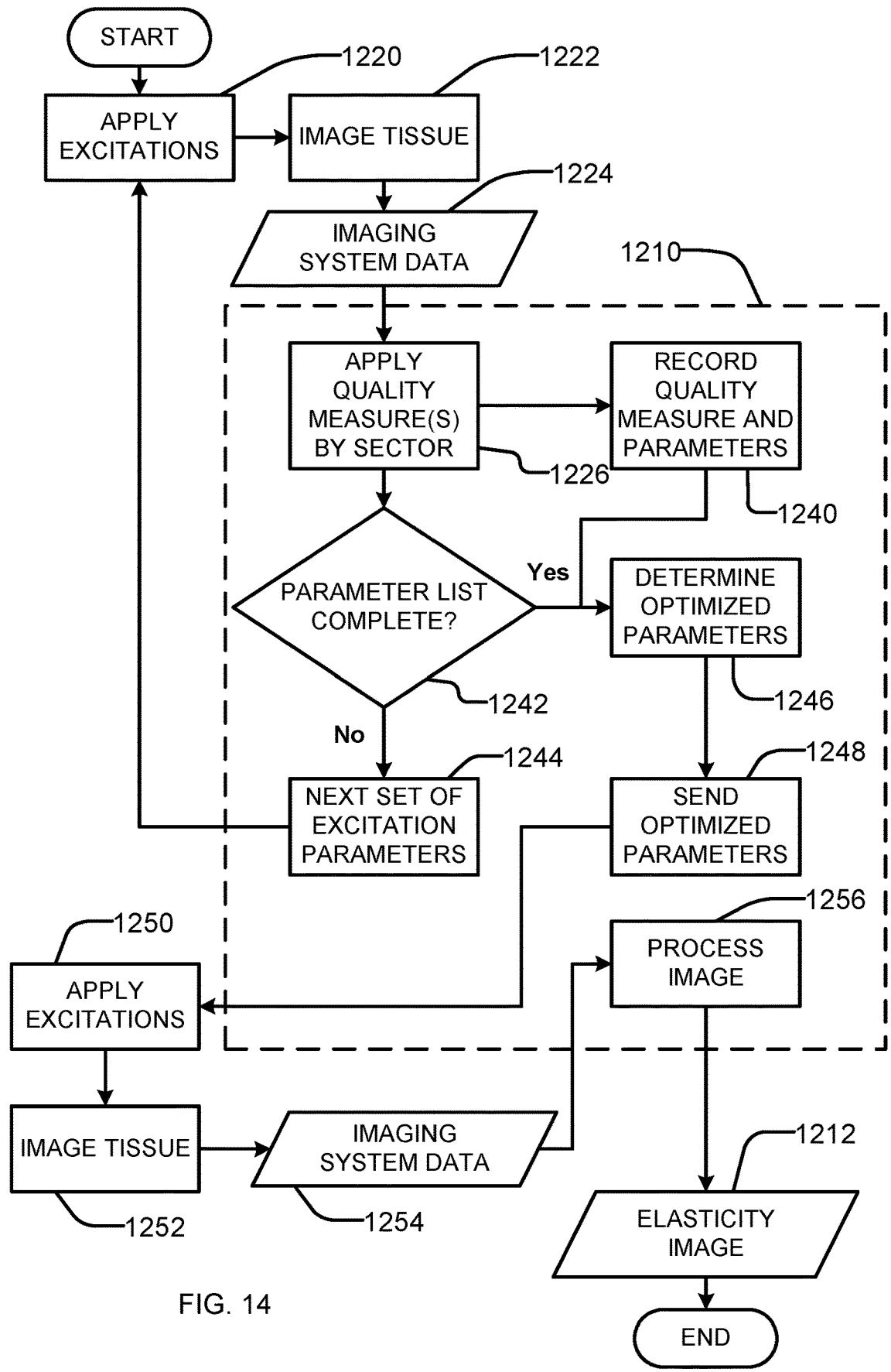
FIG. 14 is a high level flow diagram r or a method that may be performed by the controller of FIG. 12 according to a further embodiment.

FIG. 14 illustrates a system of operation of the controller 1210 of FIG. 12. A set of optimized parameters is determined. As in FIG. 13, exciters (not shown) apply excitations 1220 to a patient's tissue. Transducer (not shown) images tissue 1222 and produces imaging system data 1224. Controller 1210 calculates one or more quality measures by sector 1226 and records the quality measures and parameters 1240.

Controller 1210 then checks whether all the excitation parameters of a list of parameters have been run 1242. If all the parameters on the list have not been run the controller sends the next set of excitation parameters in the list 1244 to the exciters 102 (not shown). If all the excitation parameters in the list have been run then the controller uses the recorded measures of quality to determine a set of optimized parameters 1246. The optimized parameters are sent 1248 to exciters 102 which generate excitations 1250 using the optimized parameters.

Transducer 101 obtains ultrasound echo data from the tissue 1252 to produce imaging system data 1254 which is processed 1256 by the controller 1210 to produce an elasticity image 1212. In some embodiments the elasticity image and the intermediate imaging system data is continuously sent to a user interface (see FIG. 12).

The list of parameters may be programmed to include a range of practical values for a variety of patients. In some embodiments the controller may have multiple lists of parameters wherein different lists are optimized for different types of patient. For example, there may be a list of parameters that is optimized for larger patients which includes a larger range of low frequency inputs for the exciters. In some embodiments the patient may be immobilized while measurements are taken with the optimized parameters. Immobilizing the patient may include asking the patient to hold their breath for a period of time in which measurements are taken.

Determining a set of optimized parameters 1246 may include identifying one or more sets of parameters that produces no nodes in a region of tissue of interest. In an embodiment, determining a set of optimized parameters 1246 includes identifying a set of parameters for which the minimum measure of quality result across all sectors is higher than the minimum measure of quality across all sectors for any other set of parameters.

Some embodiments provide methods for imaging tissue that involve splitting an imaging plane into sectors. Motion of tissues in each sector may be sampled by repeatedly delivering pulses of ultrasound energy to the sector and receiving ultrasound echo signals from structures within the sector. This may be performed in a time period of at least ½ cycle, preferably at least 1 cycle of the excitation frequency. For example, a sector of the imaging plane may be pinged with 10 to 30 or so temporally spaced-apart ultrasound pulses. Echo signals resulting from these pulses permit motion of tissue in the sector to be measured. In some embodiments, bandpass sampling is used to analyze the shear wave motion.

In some embodiments controller 1210 is connected to receive signals from accelerometers attached to exciters 102. Such signals may be used to verify proper operation of exciters 102 and/or to control the frequencies, phases and/or amplitudes of driving signals for exciters 102. Such signals may also be applied to compensate for errors in the measurement of tissue motion that are caused by the motion induced by the exciter 102 in ultrasound transducers 101.

The present invention is not limited to elastography which uses ultrasound imaging as an imaging modality. Aspects of the invention as disclosed above may also or in the alternative be practice with other imaging modalities such as MRI imaging.

Unless the context clearly requires otherwise, throughout the description and the claims:
  "comprise", "comprising", and the like are to be construed in an inclusive sense, as opposed to an exclusive or exhaustive sense; that is to say, in the sense of "including, but not limited to";
  "connected", "coupled", or any variant thereof, means any connection or coupling, either direct or indirect, between two or more elements; the coupling or connection between the elements can be physical, logical, or a combination thereof;
  "herein", "above", "below", and words of similar import, when used to describe this specification, shall refer to this specification as a whole, and not to any particular portions of this specification;
  "or", in reference to a list of two or more items, covers all of the following interpretations of the word: any of the items in the list, all of the items in the list, and any combination of the items in the list;
  the singular forms "a", "an", and "the" also include the meaning of any appropriate plural forms.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Control systems in example embodiments of the invention (e.g. a controller 1210) may be implemented using any one of or any combination of: specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Any of these technologies may be configured to provide functionality as described herein such as, for example processing ultrasound data to determine tissue motions, processing determined tissue motions to determine tissue properties, generating images for display, controlling an external vibrator to perform optimizations as described herein, generating quality measures, performing feedback control over parameters for driving one or more exciters, etc.

Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

Where processes or blocks are presented in a given order, alternative examples may perform routines having steps, or employ systems having blocks, in a different order, and some processes or blocks may be deleted, moved, added, subdivided, combined, and/or modified to provide alternative or subcombinations. In addition, while elements are at times shown as being performed sequentially, they may instead be performed simultaneously or in different sequences. Each of these processes or blocks may be implemented in a variety of different ways. Also, while processes or blocks are at times shown as being performed in series, these processes or blocks may instead be performed in parallel, or may be performed at different times.

Certain aspects of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented using software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. Apparatus for ultrasound elastography, the apparatus comprising:
    an external vibrator comprising a patient-contacting member dimensioned to support at least a portion of the back of a patient lying on a patient-contacting surface of the patient-contacting member and at least one exciter, the at least one exciter mounted to the patient contacting member, the at least one exciter configured to cause motions of the patient-contacting member relative to the patient to generate shear waves in the patient, the exciter comprising a mass that is movable to apply inertial forces to the patient-contacting member whereby net inertial forces from the at least one exciter cause motions of the patient-contacting member that generate the shear waves in the patient;
    the external vibrator placeable on a bed mattress that supports the external vibrator while allowing the motions of the patient-contacting member;
    an ultrasound imaging system comprising an ultrasound transducer, driving circuits operative to drive the ultrasound transducer to transmit ultrasound pulses and to receive ultrasound echo signals;
    a controller configured to:
        process the ultrasound echo signals to:
            detect and measure tissue displacements corresponding to shear waves generated by the external vibrator; and
            identify shear wave nodes located in a volume of interest by identifying shear wave node volumes having a size and shape within the volume of interest in which a maximum tissue motion is below a threshold;
        compute a measure of quality of at least one of the measured tissue displacements;
        control the external vibrator to vary frequency, phase and/or amplitude of the shear waves based at least in part on the measure of quality; and
        control one or more operating parameters of the external vibrator in a manner that causes the shear wave nodes to move wherein the one or more operating parameters of the external vibrator comprise one or more of: a frequency of operation of one or more exciters of the at least one exciter, a relative phase of operation of first and second exciters of the at least one exciter, an amplitude of operation of one or more exciters of the at least one exciter, and a direction of vibration of one or more exciters of the at least one exciter.

2. The apparatus according to claim 1 wherein the patient-contacting member has dimensions in the range of 40 to 60 cm in a direction transverse to the mattress and 10 to 20 cm in a direction along the mattress.

3. The apparatus according to claim 2 wherein the patient-contacting member comprises a honeycomb core reinforced on top and bottom faces with sheets of a fiber reinforced plastic material.

4. The apparatus according to claim 1 wherein the patient-contacting member comprises a honeycomb core reinforced on top and bottom faces with sheets of a fiber reinforced plastic material.

5. The apparatus according to claim 1 wherein the patient-contacting member is formed with a curvature.

6. The apparatus according to claim 1 wherein the patient-contacting member comprises adjustable bolsters or supports that project on a top side of the patient-contacting member and are engageable against opposed sides of the ribcage of a patient lying on the patient-contacting member.

7. The apparatus according to claim 1 wherein the patient-contacting member comprises one or more accelerometers operable to quantify the acceleration or velocity or displacement of the patient-contacting member.

8. The apparatus according to claim 1 wherein the at least one exciter is configured to generate the inertial forces by moving a counterweight linearly or rotationally.

9. The apparatus according to claim 1 wherein the ultrasound transducer is supported by a remote centre of rotation mechanism that allows rotation of an imaging plane of the ultrasound transducer without changing a point of contact of the ultrasound transducer with the patient.

10. The apparatus according to claim 1 wherein the controller is configured to synchronize timing of operation of the ultrasound imaging system with vibrations of the external vibrator.

11. The apparatus according to claim 1 wherein the at least one exciter comprises the first and second exciters, wherein the first and second exciters are configured to generate inertial forces directed in different directions and a phase of the motion of a first mass of the first exciter relative to the phase of the motion of a second mass of the second exciter is adjustable to cause a direction of the net inertial force on the patient-contacting member to change.

12. The apparatus according to claim 1 wherein the net inertial force comprises plural frequencies in the range of 45 to 70 Hz.

13. The apparatus according to claim 1 wherein the controller is connected to deliver driving signals to the at least one exciter and to adjust the driving signals in a closed-loop in response to feedback received at least in part by way of the ultrasound imaging system, the controller configured to compute the quality measure of tissue displacements and/or a measurement wavelength of shear waves in a plane of ultrasound imaging in real-time and to adjust operation of the at least one exciter to move or eliminate low displacement nodes having maximum tissue motion that is less than 100 microns and/or optimize the shear wave direction and amplitude.

14. The apparatus according to claim 1 wherein the quality measure comprises a signal to noise ratio.

15. The apparatus according to claim 1 wherein the quality measure comprises an indication of whether a magnitude of a phasor representing the shear waves is outside of a range between a minimum magnitude and a maximum magnitude.

16. The apparatus according to claim 1 wherein the controller is configured to optimize shear wave direction relative to a plane of imaging by the ultrasound transducer by:
processing the ultrasound echo signals to determine an apparent wavelength of shear waves and adjusting the one or more operating parameters of the external vibrator in a manner that causes the apparent wavelength of the shear waves to be reduced, wherein the one or more operating parameters of the external vibrator comprise one or more of: the frequency of operation of one or more exciters of the at least one exciter, the relative phase of operation of the first and second exciters of the at least one exciter, the amplitude of operation of one or more exciters of the at least one exciter, and the direction of vibration of one or more exciters of the at least one exciter.

17. The apparatus according to claim 16 wherein the controller is configured to control the one or more operating parameters of the external vibrator in real time as the orientation of the ultrasound transducer is changed to minimize the apparent wavelength of the shear waves for each orientation of the ultrasound transducer.

18. The apparatus according to claim 1 wherein the at least one exciter comprises a plurality of exciters and the controller is connected to drive the plurality of exciters and to adjust shear wave direction in a target volume of tissue to be imaged by monitoring ultrasound images of the target volume to determine an apparent wavelength of the shear waves and adjusting phases of the plurality of exciters to minimize the apparent wavelength of the shear waves.

19. The apparatus according to claim 1 wherein the controller is configured to process a sequence of ultrasound images of the target volume to identify any regions of tissue displacements by the shear waves that are below a threshold displacement level and, if such regions are found, automatically adjust the frequency or frequencies and/or phases and/or amplitudes of driving signals being delivered to the at least one exciter to determine if a set of frequency or frequencies and/or phases and/or amplitudes of the driving signals can be found in which the possible nodes are gone or moved to another location.

20. The apparatus according to claim 1 wherein the controller is configured to generate colour elastography images which indicate areas in which imaged tissues have different mechanical properties by different colours and the apparatus comprises a display connected to display the elastography images.

21. The apparatus according to claim 1 wherein the inertial forces comprise a force component that has a direction which is parallel to the patient-contacting surface of the patient-contacting member.

22. The apparatus according to claim 1 wherein the mass of the at least one exciter is movable in a direction substantially parallel to a plane of the patient contacting member.

* * * * *